United States Patent
Small et al.

(10) Patent No.: US 9,387,263 B2
(45) Date of Patent: Jul. 12, 2016

(54) RBAP48 TRANSGENIC MICE FOR DRUG DISCOVERY IN AGE-RELATED MEMORY DECLINE

(75) Inventors: Scott A. Small, Millerton, NY (US); Ilias Pavlopoulos, New York, NY (US); Eric R. Kandel, Riverdale, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 32 days.

(21) Appl. No.: 14/236,945

(22) PCT Filed: Aug. 2, 2012

(86) PCT No.: PCT/US2012/049385
§ 371 (c)(1),
(2), (4) Date: Jun. 18, 2014

(87) PCT Pub. No.: WO2013/022715
PCT Pub. Date: Feb. 14, 2013

(65) Prior Publication Data
US 2014/0294798 A1    Oct. 2, 2014

Related U.S. Application Data

(60) Provisional application No. 61/515,807, filed on Aug. 5, 2011.

(51) Int. Cl.
| | |
|---|---|
| *A01K 67/00* | (2006.01) |
| *G01N 33/00* | (2006.01) |
| *A61K 49/00* | (2006.01) |
| *C07K 14/47* | (2006.01) |
| *C12N 15/85* | (2006.01) |
| *A01K 67/027* | (2006.01) |
| *A61K 31/353* | (2006.01) |
| *A61K 38/45* | (2006.01) |

(52) U.S. Cl.
CPC ......... *A61K 49/0008* (2013.01); *A01K 67/0275* (2013.01); *A61K 31/353* (2013.01); *A61K 38/45* (2013.01); *C07K 14/47* (2013.01); *C12N 15/8509* (2013.01); *A01K 2217/00* (2013.01); *A01K 2217/056* (2013.01); *A01K 2217/203* (2013.01); *A01K 2227/105* (2013.01); *A01K 2267/0318* (2013.01); *C12N 2830/003* (2013.01)

(58) Field of Classification Search
USPC ....................................... 800/3, 18
See application file for complete search history.

(56) References Cited

U.S. PATENT DOCUMENTS

2009/0253779 A1    10/2009    Small

OTHER PUBLICATIONS

Jones, "Histone acetylation and the aging hippocampus", Ph.D. thesis, Columbia University, abstract, 2010.*
Peleg, Science, 2010, vol. 328, No. 5979, p. 753-756.*
Jones (2010). Histone Acetylation and the Aging Hippocampus. Ph.D. Thesis Columbia University, 1-148 [Abstract].
Peleg et al. (2010). Altered Histone Acetylation Is Associated with Age-Dependent Memory Impairment in Mice. *Science*, 328(5979), 753-756.
Levenson & Sweatt (2005). Epigenetic Mechanisms in Memory Formation. *Nature Reviews Neuroscience*, 6, 108-118.
Hasegawa at al. (2009). Transgenic up-regulation of alpha-CaMKII in forebrain leads to increased anxiety-like behaviors and aggression. *Molecular Brain*, 2(6), 1-11.
Notification of Transmittal of the International Search Report and the Written Opinion of the International Searching Authority, or the Declaration, including an International Search Report and Written Opinion of the International Searching Authority, mailed Jan. 28, 2013 in connection with PCT International Application No. PCT/US2012/049385, filed Aug. 2, 2012.

* cited by examiner

*Primary Examiner* — Michael Wilson
(74) *Attorney, Agent, or Firm* — John P. White; Cooper & Dunham LLP

(57) ABSTRACT

Described is a transgenic mouse with two transgenes, each of which transgene comprises a DNA sequence encoding a dominant negative form of RbAp48 protein, wherein the expression of the dominant negative form of RbAp48 is spatially restricted to the forebrain by a CaM Kinase IIa promoter and wherein the expression of the dominant negative form of RbAp48 is controlled by tetracycline-controlled transcriptional activation. Also provided are methods for evaluating in the transgenic mouse the potential therapeutic effect of an agent for slowing, inhibiting or preventing age-related memory decline in a mammalian subject.

14 Claims, 14 Drawing Sheets

Fig. 2a
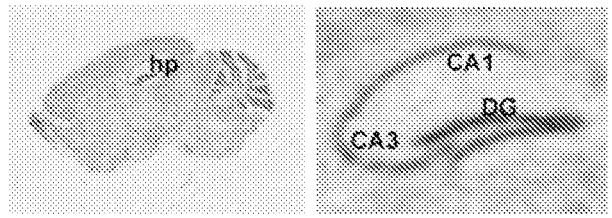
Fig. 2b
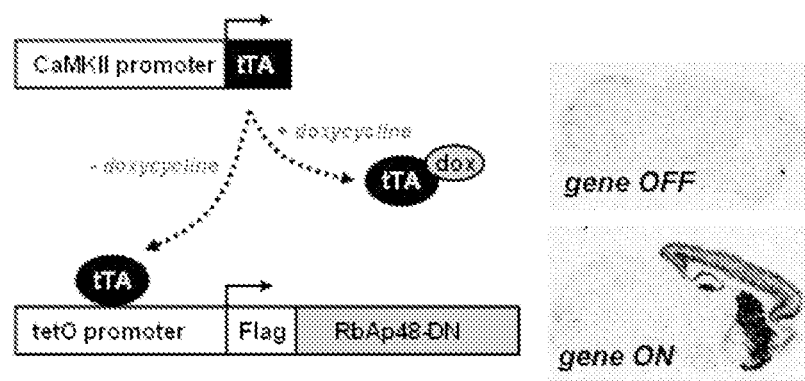
Fig. 2c
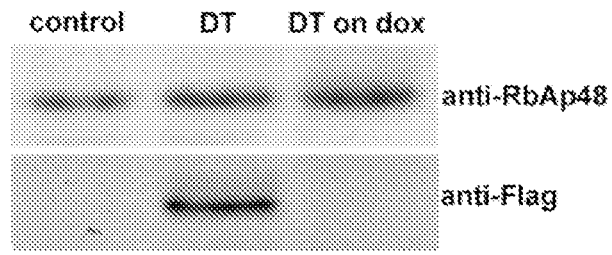
Fig. 2d
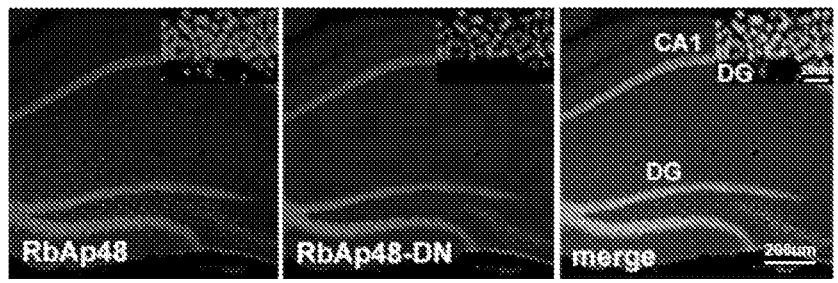
Figures 2a-2d Fig. 4a
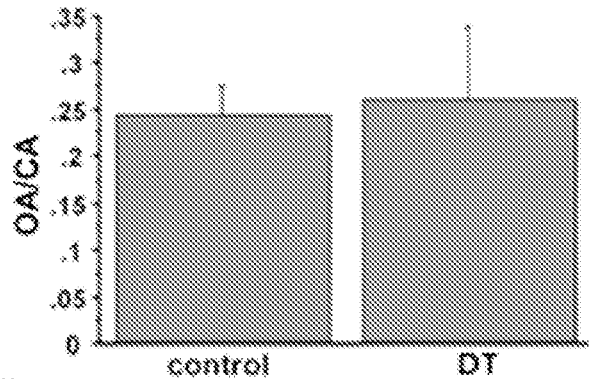
Fig. 4b
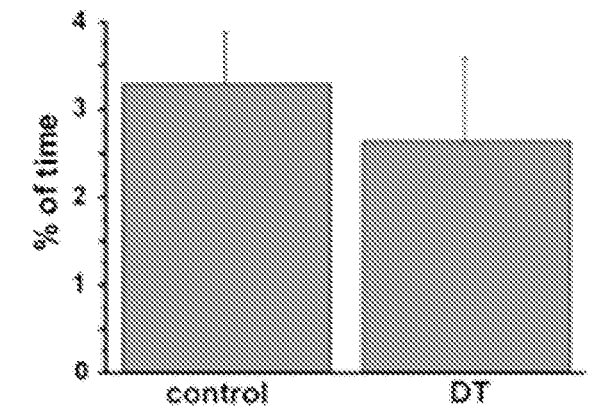
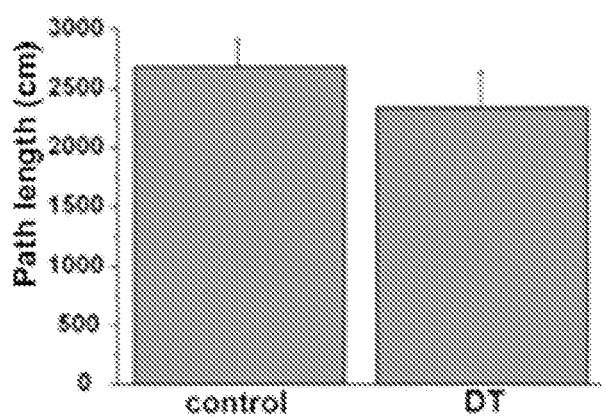
Figures 4a-4b Fig. 5a
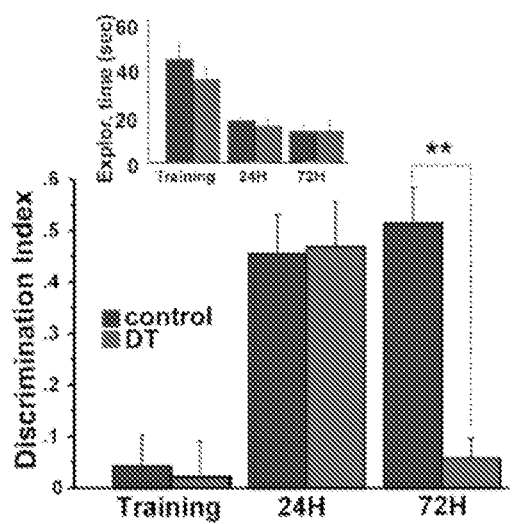
Fig. 5b
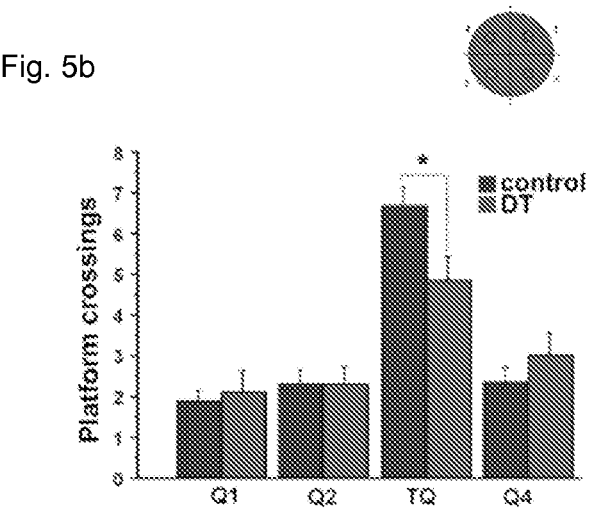
Fig. 5c
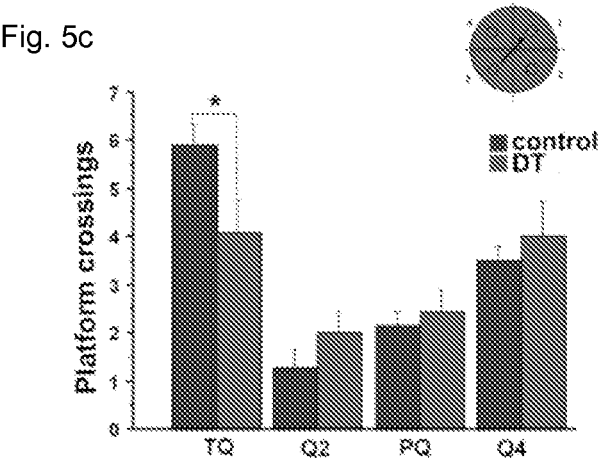
Figures 5a-5c Fig. 6a
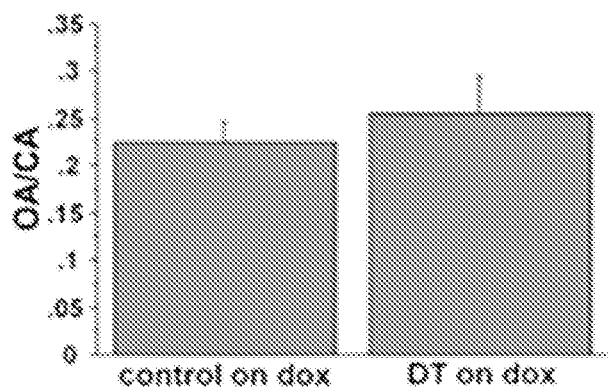
Fig. 6b
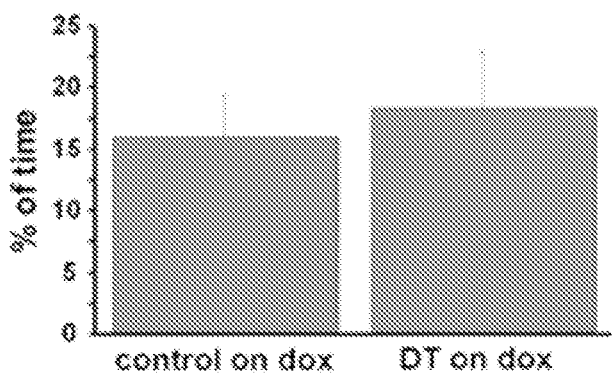
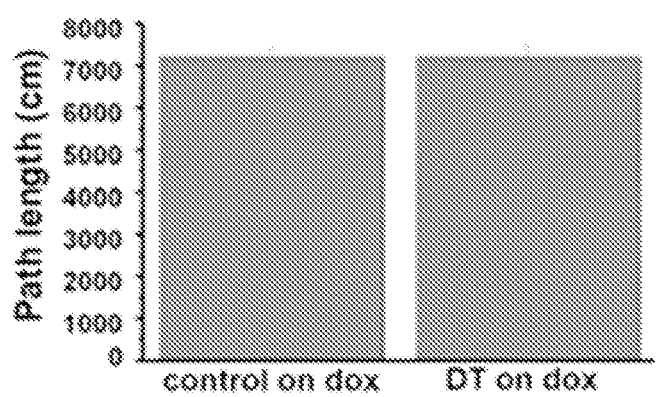
Figures 6a-6b Fig. 8a
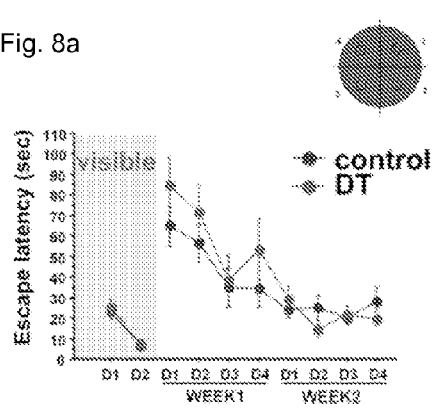
Fig. 8c
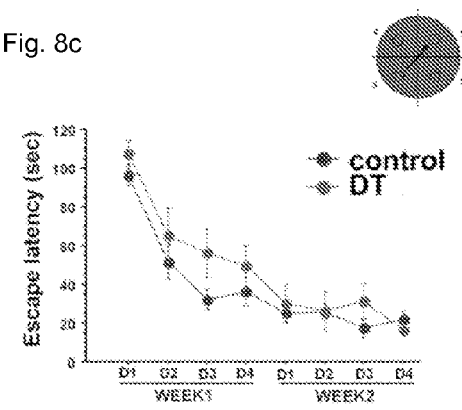
Fig. 8b
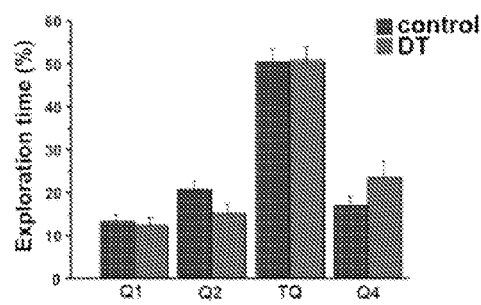
Fig. 8d
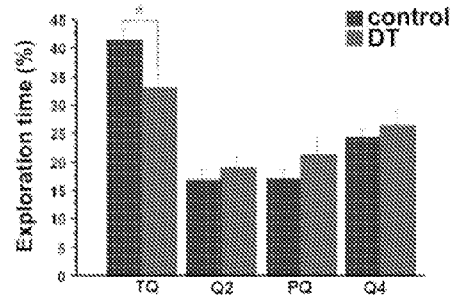
Figures 8a-8d Fig. 9a
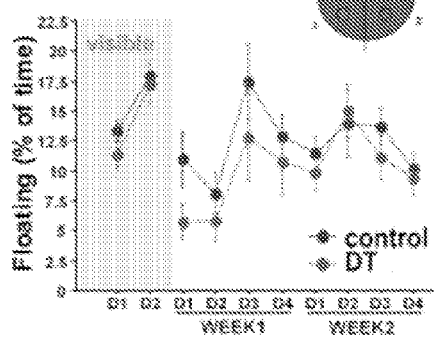
Fig. 9d
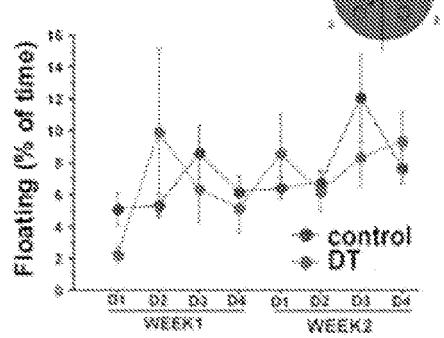
Fig. 9b
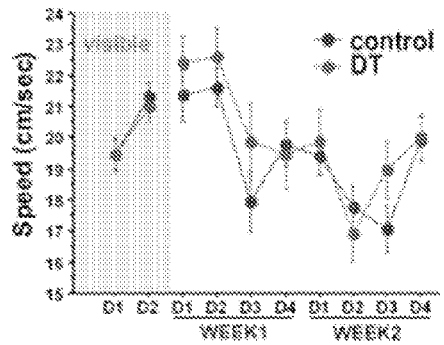
Fig. 9e
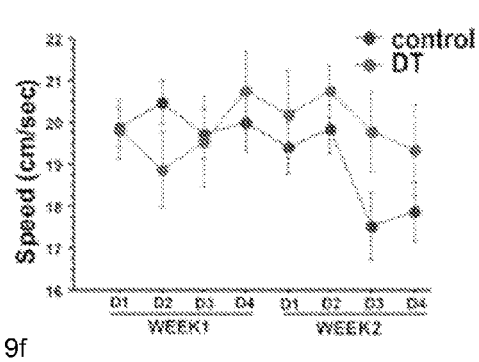
Fig. 9c
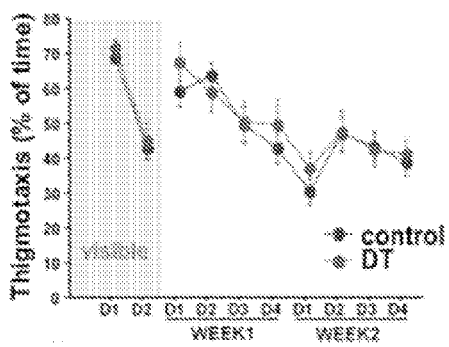
Fig. 9f
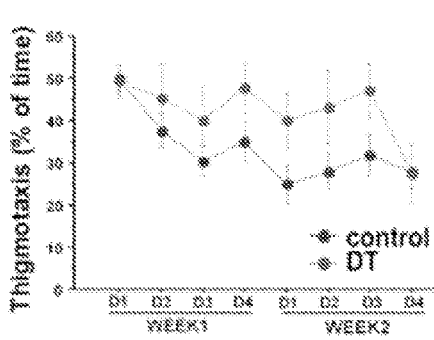
Figures 9a-9f Fig. 10a
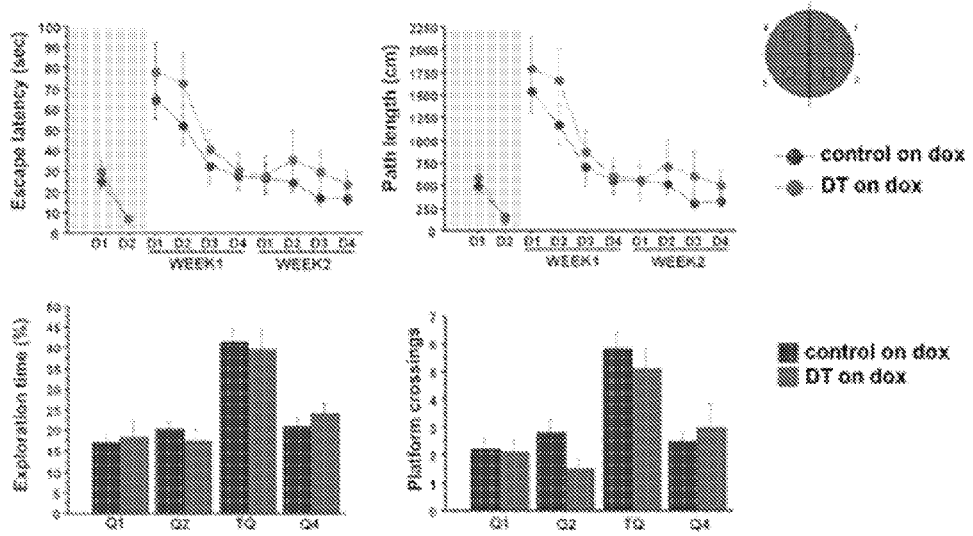
Fig. 10b
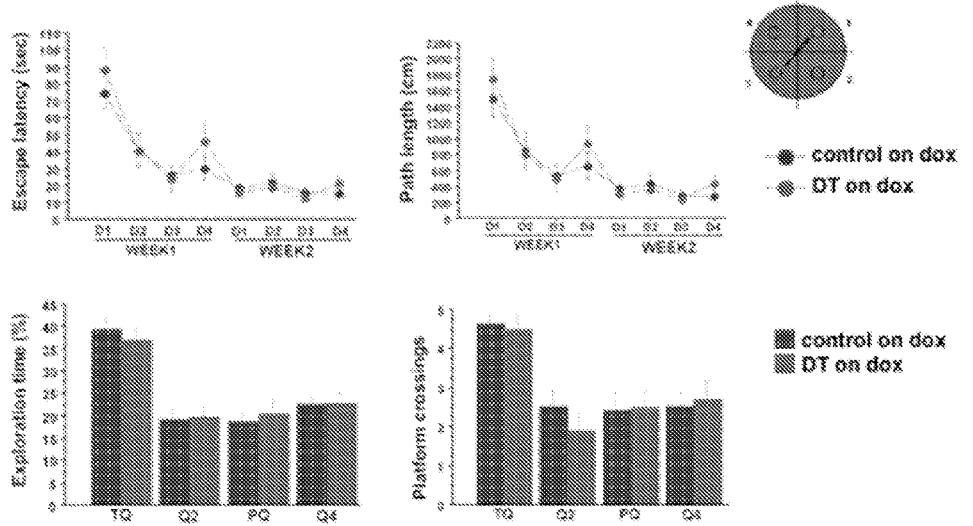
Figures 10a-10b Fig. 11a
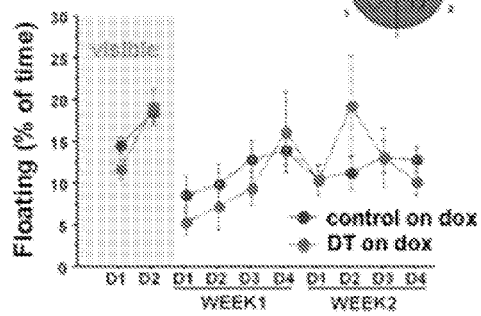
Fig. 11d
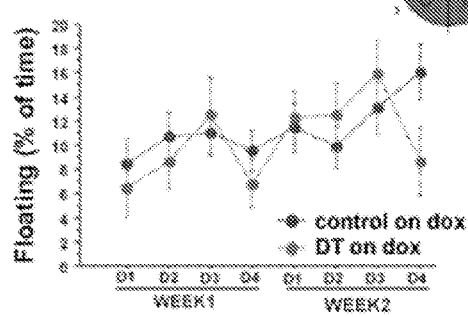
Fig. 11b
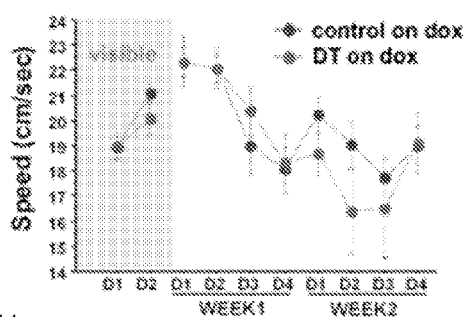
Fig. 11e
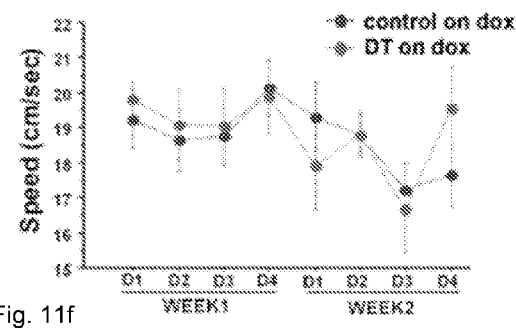
Fig. 11c
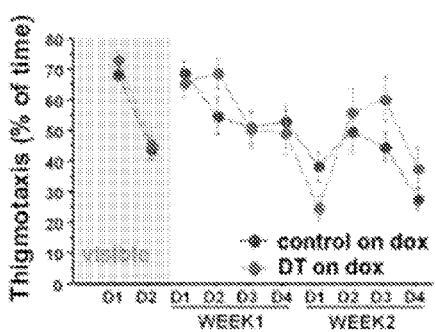
Fig. 11f
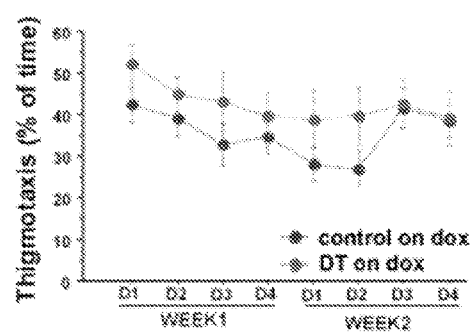
Figures 11a-11f Fig. 12a
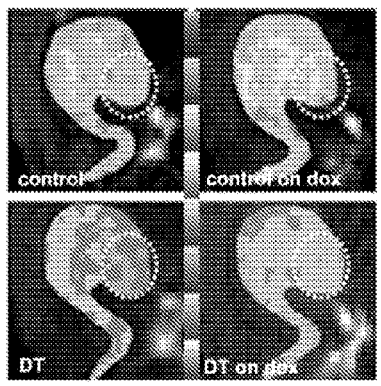
Fig. 12b
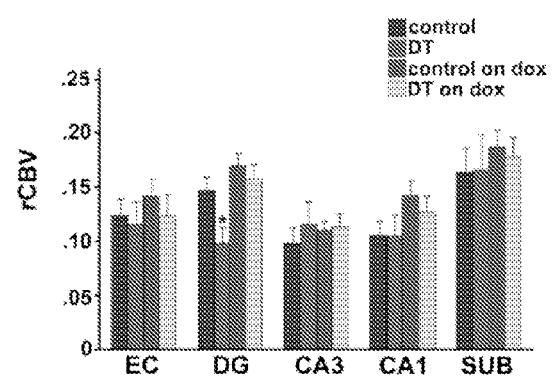
Fig. 12c
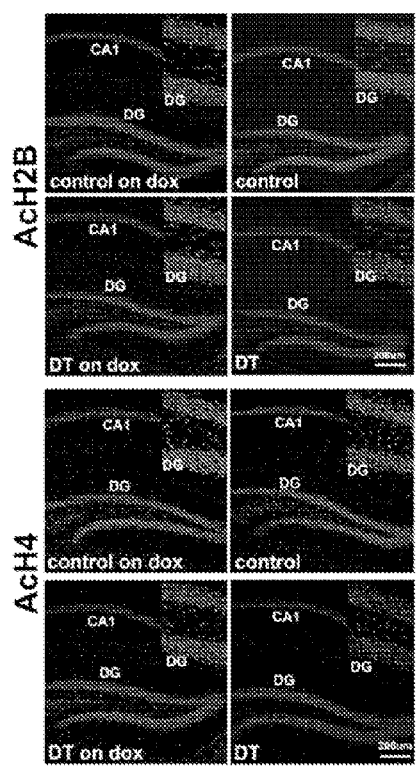
Fig. 12d
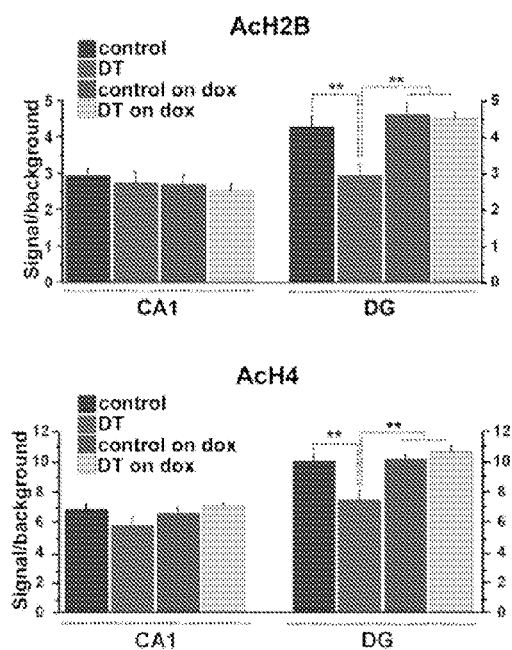
Figures 12a-12d

RBAP48 TRANSGENIC MICE FOR DRUG DISCOVERY IN AGE-RELATED MEMORY DECLINE

CROSS-REFERENCE TO RELATED APPLICATIONS

This application is a § 371 national stage of PCT International Application No. PCT/US2012/049385, filed Aug. 2, 2012, claiming the benefit of U.S. Provisional Application No. 61/515,807, filed Aug. 5, 2011, the contents of each of which are hereby incorporated by reference in their entirety.

REFERENCE TO SEQUENCE LISTING

This application incorporates-by-reference nucleotide and/or amino acid sequences which are present in the file named "140204_0575_82729_A_PCT_US Substitute_Sequence_Listing_BI.txt," which is 4.26 kilobytes in size, and which was created Feb. 3, 2014 in the IBM-PC machine format, having an operating system compatibility with MS-Windows, which is contained in the text file filed Feb. 4, 2014 as part of this application.

Throughout this application, certain publications are referenced. Full citations for these publications, as well as additional related references, may be found immediately preceding the claims. The disclosures of these publications are hereby incorporated by reference into this application in order to more fully describe the state of the art as of the date of the invention described and claimed herein.

BACKGROUND OF THE INVENTION

The function of the hippocampal formation, a brain structure vital for memory, declines in later life, and in humans the dominant causes are Alzheimer's disease (AD) and the aging process itself[1]. The hippocampal formation is circuit that is made up molecularly distinct subregions[2] and this molecular anatomy accounts for why hippocampal subregions are differentially vulnerable to pathogenic mechanisms. Because of circuit properties, dysfunction in one subregion can affect others, and studies have mapped distinct spatiotemporal patterns of dysfunction in the hippocampal circuit that dissociate AD from aging. In AD, these maps have identified the EC as the subregion differentially affected by the disease[3-5] while the dentate gyrus and CA3 are relatively preserved[3,4,6], a pattern that has been confirmed in vivo by high-resolution variants of fMRI[7-9]. In contrast, the EC is relatively preserved in aging, which appears to target other subregions instead. A growing number of high-resolution fMRI[8-10] and recent cognitive studies[11-14] have, in particular, implicated the DG in aging. Furthermore, in contrast to AD, the effect of aging on hippocampal function begins in at a relatively young age and progresses monotonically across the lifespan[8-10,15].

SUMMARY OF THE INVENTION

This invention provides a transgenic mouse comprising two transgenes, each of which transgene comprises a DNA sequence encoding a dominant negative form of RbAp48 protein, wherein the expression of the dominant negative form of RbAp48 is spatially restricted to the forebrain by a CaM Kinase IIa promoter and wherein the expression of the dominant negative form of RbAp48 is controlled by tetracycline-controlled transcriptional activation.

This invention also provides a method for evaluating in a transgenic mouse the potential therapeutic effect of an agent for slowing, inhibiting or preventing age-related memory decline in a mammalian subject, which method comprises: (a) administering the agent to the transgenic mouse provided herein, wherein expression of the dominant negative form of RbAp48 is activated prior to administering the agent to the transgenic mouse; (b) determining, after a suitable period of time, the memory function of the transgenic mouse of step (a), wherein an increase in the memory function determined in step (b) as compared to the memory function determined in a transgenic mouse provided herein expressing the dominant negative form of RbAp48 to which the agent has not been administered indicated that the agent has a potential therapeutic effect for slowing, inhibiting or preventing age-related memory decline in the mammalian subject.

This invention further provides a method for evaluating in a transgenic mouse the potential therapeutic effect of an agent for slowing, inhibiting or preventing age-related memory decline in a mammalian subject, which method comprises: (a) administering the agent to the transgenic mouse provided herein, wherein expression of the dominant negative form of RbAp48 is activated prior to administering the agent to the transgenic mouse; (b) measuring, after a suitable period of time, the cerebral blood volume (cbv) in the dentate gyrus of the transgenic mice of step (a); wherein an increase in cbv measured in step (b) as compared to the cbv measured in a transgenic mouse provided herein expressing the dominant negative form of RbAp48 to which the agent has not been administered indicates that the agent has a potential therapeutic effect for slowing, inhibiting or preventing age-related memory decline in the mammalian subject.

Provided herein is also a method for treating a subject afflicted with age-related memory decline comprising administering to the subject a therapeutically effective amount of an agent which increases the expression of RbAp48 protein in the cells of the subject's brain, wherein the agent is selected from the group consisting of epicatechin.

Further provides is a method for treating a subject afflicted with age-related memory decline comprising administering to the subject a therapeutically effective amount of an agent which inhibits the deactylation of histones in the dentate gyrus of the subject, thereby treating the subject afflicted with the age-related memory decline.

Finally, this invention provides a method for treating a subject afflicted with age-related memory decline comprising administering to the subject a therapeutically effective amount of an agent which increase the acetylation of histones in the dentate gyrus of the subject, thereby treating the subject afflicted with the age-related memory decline.

BRIEF DESCRIPTION OF THE FIGURES

FIGS. 2a-2d. Generation and characterization of double-transgenic mice expressing RbAp48-DN in their forebrain: (FIG. 2a) $^{33}$P-labelled oligonucleotide in situ hybridization analysis of RbAp48 mRNA expression on coronal brain slices from adult (3½ months) wild type mice. RbAp48 mRNA is mostly expressed in the hippocampus (Hp) with the highest levels of expression in the dentate gyrus (DG). (FIG. 2b) Schematic representation of doxycycline regulated expression of RbAp48-DN transgene restricted in the forebrain. Right panel: In situ hybridization analysis of RbAp48-DN mRNA on sagittal brain sections from adult (day P95) double-transgenic animals either off dox (gene on) or on dox (gene off). (FIG. 2c) Western blots showing the expression of RBAp48-DN (anti-Flag) and endogenous RbAp48 proteins in the hippocampus of 95-day-old double-transgenic animal (DT). DT mouse on dox and tetO -RbAp48-DN single transgenic mouse (control) are negative controls. (FIG. 2d) Confocal optical sections of the hippocampus from adult DT mouse. Co-immunostaining using anti-RbAp48 (detection of endogenous RbAp48) and anti-Flag antibodies (detection of RbAp48-DN) show that both proteins are expressed in the same neurons and exhibit nuclear localization. DG: Dentate gyrus.

FIG. 4: Data from the elevated plus maze (a) and an open field (b) of mice tested off dox (a) Averaged ratio (±SEM) of the time spent in open-arms versus closed-arms is shown. DT mice off dox (DT; RbAp48-DN expression) and control animals off dox (control) spent comparable time in the closed and open arms of the maze (ANOVA revealed no genotype effect; $F_{(1,31)}=0.056$, $p=0.815$). (b) Percentage of time spent in the center of the open field and total path length (±SEM). Both groups of mice exhibited similar performance (ANOVA; $F_{(1,31)}=0.377$, $p=0.543$ and $F_{(1,31)}=0.803$, $p=0.377$ for time spent in the center and path length, respectively).

FIGS. 5a-5c Expression of RbAp48-DN in the adult forebrain causes hippocampal-dependent memory deficits: (FIG. 5a) Data from novel object recognition task of the same group of mice. The mean discrimination index (±SEM) is shown. The DT mice performed worse during the 72-hour memory test (significant genotype and genotype*test effects from repeated measures ANOVA; $F_{(1,31)}=6.95$, $p=0.013$ & $F_{(2,62)}=5.267$, $p=0.0077$, respectively; t test for 72-hour test **$p=0.0001$]. Inset: total exploration time±SEM. No differences were observed for total exploration time (repeated measure ANOVA; no genotype or genotype*session effects: $F_{(1,31)}=0.503$, $p=0.4834$; $F_{(2,62)}=0.543$, $p=0.5837$, respectively). (FIGS. 5b & 5c) Data from the Morris water maze from a group of mice that was kept off dox (RbAp48-DN transgene on) during the task. The number of platform crossings (±SEM) during probe trials one day after the end of acquisition (FIG. 5b) and the transfer phase (FIG. 5c) is shown [DT=11; controls (pooled)=22 (single tetO=6, single tTA=8, wild type=8)]. The DT mice displayed significantly reduced performance in the training quadrant (TQ) compared to controls (respectively for b and c: repeated-measures ANOVA; quadrant*genotype interaction effects: $F_{(3,93)}=2.748$, $p=0.04$; $F_{(3,93)}=3.023$, $p=0.03$; t test in TQ: $p=0.017$ and $p=0.035$). PQ: Previous training quadrant (TQ in b). *$p<0.036$.

FIGS. 6a and 6b: Data from the elevated plus maze (a) and an open field (b) of mice tested on dox (FIG. 6a) Averaged ratio (±SEM) of the time spent in open-arms (OA) versus closed-arms (CA) is shown. No differences were observed for DT mice on dox (n=10) and controls on dox [n=17 (pooled); single tetO: 5, single tTA: 5 and WT: 7]. ANOVA revealed no genotype effect ($F_{(1,25)}=0.550$, $p=0.4651$). (FIG. 6b) Percentage of time spent in the center of the open field and total path length (±SEM). Similar performance was observed between both groups of animals (ANOVA; $F_{(1,25)}=0.162$, $p=0.691$ and $F_{(1,25)}=0.003$, $p=0.9594$ for time spent in the center and path length, respectively).

FIGS. 8a-8d: Data from the Morris water maze from a group of mice that was kept off dox during the task (FIGS. 8a and 8b) and data from the same group of mice tested in the transfer phase of the water maze task (FIG. 8c and FIG. 8d). (FIG. 8a) The mean escape latency and path length (±SEM) for mice to reach the platform in the visible and the hidden version of the water maze are plotted against the day of the experiment [DT=11; controls (pooled)=22 (single tetO=6, single tTA=8, wild type=8)]. The escape latencies and path lengths were similar among controls and double-transgenic (DT) mice in the visible version of the task (repeated-measures ANOVA for escape latencies and path lengths; training day effect: All $Fs_{(1,31)} \geq 16,08$, $p<0.0001$; genotype effect: All $Fs_{(1,31)} \leq 0.5$, $p \geq 0.047$). In the hidden version of the task, the DT animals displayed similar performance to their control siblings during acquisition (repeated measures ANOVA; latency: $F_{(1,31)}=1.77$, $p=0.193$ and path length: $F_{(1,31)}=1.695$, $p=0.2025$). Both groups of mice had learned the task by the end of training (repeated-measures ANOVA for day effect for latencies and path lengths; controls: all $Fs_{(7,147)}>4.5$, $p \leq 0.0001$; DT mice: all $Fs_{(7,70)}>6.2$, $p<0.0001$). (FIG. 8b) Probe trial performance one day after the end of training (week2/day5). Percentage of time spent in quadrants (±SEM) is shown. DT and control mice spent similar time in the training quadrant (TQ) [repeated-measures ANOVA did not reveal significant genotype effect ($F_{(1,31)}=0.036$, $p=0.85$) or genotype*quadrant interaction effect ($F_{(3,93)}=1.415$, $p=0.2434$)]. However, the DT mice formed a less accurate knowledge of the platform location. (FIG. 8c) DT and control animals displayed similar performance during training (repeated-measures ANOVA for genotype effect; $F_{(1,31)}=2.75$, $p=0.107$ for escape latency & $F_{(1,31)}=2.32$, $p=0.138$ for path length). (FIG. 8d) During a probe trial one day after the end of training (week2/day 5), the DT mice performed worse than the controls in the training quadrant [repeated-measures ANOVA; genotype*quadrant interaction effect: $F_{(3,93)}=3.201$, $p=0.0269$; t test for new training quadrant: *$p=0.012$].

FIGS. 9a-9f: Comparison of non-cognitive parameters during the hidden (a-c) or the transfer phase (d-f) of the Morris water maze task of mice tested off dox Floating, speed and thigmotaxis (±SEM) across days are shown. Repeated-measures ANOVA did not reveal significant genotype effect [Visible platform: All $Fs_{(1,31)}<1.4$, $p=0.2453$ (floating), $p=0.7991$ (speed) & $p=0.4366$ (thigmotaxis); Hidden platform: All $Fs_{(1,31)}<4.1$, $p=0.0745$ (floating), $p=0.2567$ (speed) $p=0.3855$ (thigmotaxis); Tranfer: All $Fs_{(1,31)}<3.3$, $p=0.8263$ (floating), $p=0.4777$ (speed) & $p=0.0787$ (thigmotaxis)].

FIG. 10: Data from Morris water maze from a group of animals kept on dox during the task (blockade of RbAp48-DN expression in adulthood). The escape latencies and path lengths (±SEM) across days in the visible (a), the hidden version (a) and the transfer phase (b) of the water maze are shown [DT-on dox, n=10; controls on dox (pooled), n=17

Figure 1:
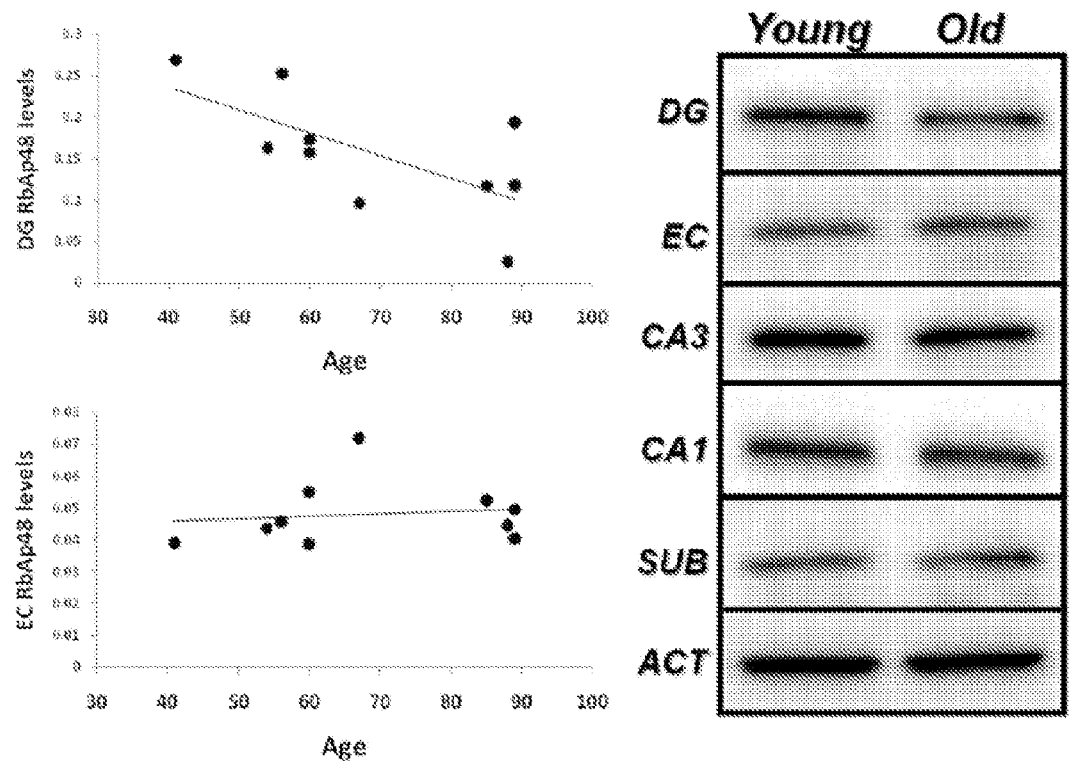
FIG. 1. RbAp48 deficiency isolated from the aging human hippocampal formation: An age-related decrease in RbAp48 protein levels (normalized by actin) is observed in the dentate gyrus (DG) (left upper scatter plot) but not the entorhinal cortex (EC) (left lower scatter plot). The blots show an example of RbAp48 levels measured from a young and old sample in the dentate gyrus (DG), entorhinal cortex (EC), the CA3 and CA1 subregion and the subiculum (SUB). Lower panel shows actin (Act) levels measured from the dentate gyrus of the young and old sample.

(single tetO=5, single tTA=5, wild type=7)]. The exploration time and platform crossings (±SEM) during probe trials are also shown. (a) DT and control animals on dox displayed similar performance during the acquisition phase of the hidden platform version of the water maze task [repeated-measures ANOVA for escape latency and path length revealed significant effect of training day (p<0.0001) but not genotype ($F_{(1,25)}$=0.290, p=0.1427 and ($F_{(1,25)}$=0.562, p=0.1645, respectively)]. Both groups exhibited similar exploration time and platform crossings in the training quadrant during probe trial at the end of training (week2/day5; repeated-measures ANOVA did not reveal significant genotype*quadrant interaction effect; $F_{(3,75)}$=0.385, p=0.7639 and ($F_{(3,25)}$=1.119, p=0.3470, exploration time and platform crossings, respectively). (b) The inhibition of RbAp48-DN expression in the double transgenic animals reversed also the memory deficits in the transfer phase. Both DT and control animals tested on dox learned equally well the new platform location and reached comparable minimal escape latencies and path lengths at the end of training [repeated-measures ANOVA for escape latency and path length revealed significant effect of training day (p<0.0001) but not of genotype ($F_{(1,25)}$=0.507, p=0.4829 and $F_{(1,25)}$=0.245, p=0.6253 for escape latency and path length, respectively)]. A probe trial at the end of training (week2/day5) showed that both control and double transgenic mice on dox acquired a good memory for the new platform location and exhibited similar exploration time and platform crossings in the training quadrant (repeated-measures ANOVA; no significant genotype*quadrant interaction effect: $F_{(3,75)}$=0.221, p=0.8813 and $F_{(3,75)}$=0.375, p=0.7716, exploration time and platform crossings, respectively). These results confirm that the memory deficits in the RbAp48-DN expressing mice do not have any developmental aetiology and does not result from position effects of the transgenes.

FIG. 11: Comparison of non-cognitive parameters during the hidden (a-c) and the transfer phase (d-f) of the Morris water maze task of mice tested on dox Floating, speed and thigmotaxis (±SEM) across days are shown. Repeated-measures ANOVA did not reveal significant genotype effect [Visible platform: All $Fs_{(1,25)}$<1.45, p=0.4697 (floating), p=0.2394 (speed) & p=0.4621 (thigmotaxis); Hidden platform: All $Fs_{(1,25)}$<0.74, p=0.8825 (floating), p=0.5031 (speed) & p=0.3981 (thigmotaxis); Tranfer: All $Fs_{(1,25)}$<5.35, p=0.5289 (floating), p=0.8811 (speed) & p=0.0593 (thigmotaxis)].

FIGS. 12a-12d. Within the hippocampal formation expression of RbAp48-DN differentially targets the dentate gyrus (FIG. 12a) Individual examples of cerebral blood volume (CBV) maps of the hippocampal formation, generated with magnetic resonance imaging, in double-transgenic mice (DT) on or off dox. The CBV maps are color codes such that cooler colors reflect less basal metabolism. The dentate gyrus, indicated by the circle in each map, shows relative less CBV in the double-transgenic mice off dox. (FIG. 12b) Group data analysis shows a selective decrease in the rCBV (relative cerebral blood volume) of dentate gyrus in the double-transgenic mice off dox. EC=entorhinal cortex, DG=dentate gyrus, SUB=subiculum. (FIG. 12c) Immunohistochemistry against acetylated histones H2B (lys20) and H4 (lys12) of double-transgenic and control mice either off or on dox. Insets: high magnification images of dentate gyrus (DG). (FIG. 12d) Quantification analysis of ACH2B and ACH4 (lys20 & lys12, respectively). The levels of ACH2B and ACH4 of DT mice on dox and controls on and off dox were similar (ANOVA; ACH2B; CA1: $F_{(2,69)}$=1.014, p=0.3683; DG: $F_{(2,69)}$=0.261, p=0.7707; ACH4: CA1: $F_{(2,62)}$=0.419, p=0.6598; DG: $F_{(2,62)}$=0.452, p=0.6382). RbAp48-DN expressing mice (DT off dox) displayed significantly reduced levels of ACH2B and ACH4 in their DG compared to all of the controls (ANOVA; ACH2B: $F_{(3,95)}$=5.069, p=0.0027; ACH4: $F_{(3,83)}$=7.458, p=0.0002). Despite that RbAp48-DN was expressed in the CA1 neurons, no differences were observed (ANOVA; ACH2B: $F_{(3,95)}$=0.469, p=0.7043; ACH4: $F_{(3,83)}$=2.192, p=0.0951). *p<0.05, **p<0.01.

Figure 13:
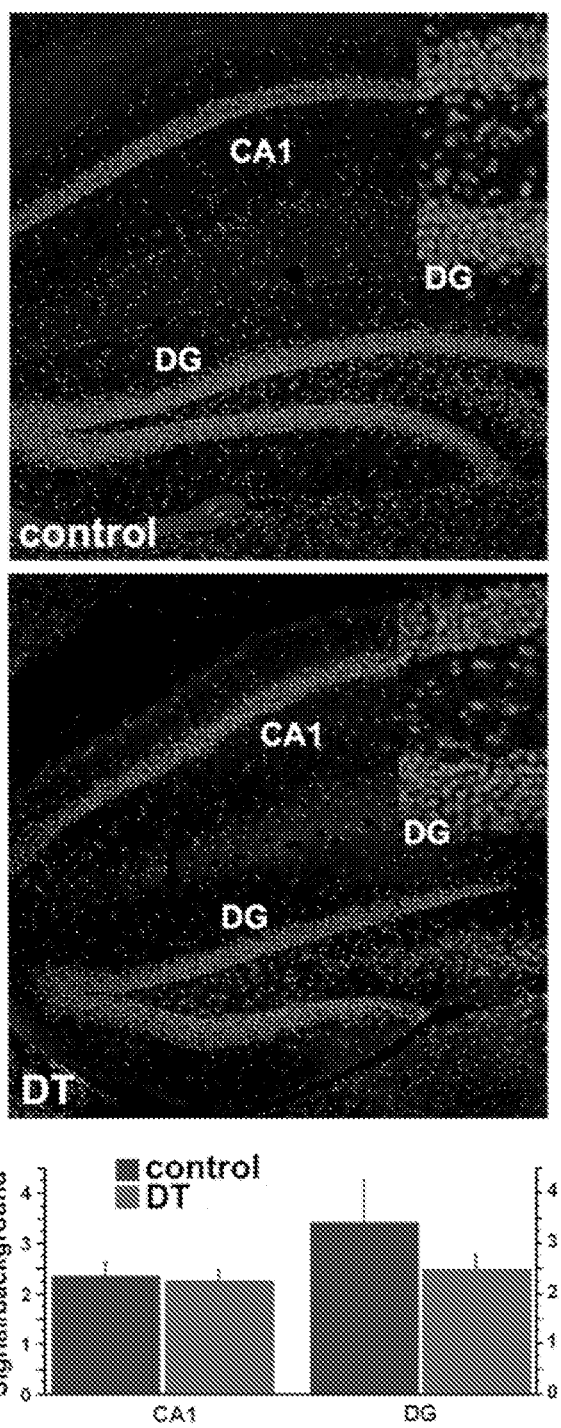

FIG. 13: Immunohistochemistry and quantification of acetylated histone H3 (lys9; Inset: high magnification images of dentate gyrus (DG). No differences were observed between double-transgenic mice off dox (DT; RbAp48-DN expressing mice) and control animals off dox (ANOVA; CA1: $F_{(1,42)}$=0.052, p=0.8214; DG: $F_{(1,42)}$=0.637, p=0.4292).

Figure 14:
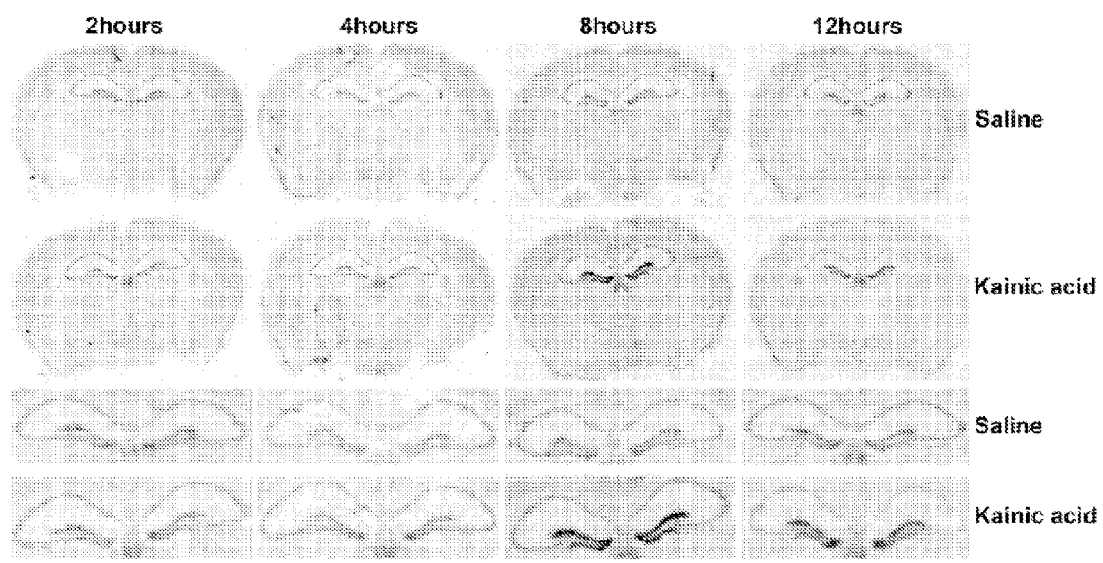

FIG. 14: RbAp48 transcript distribution in the adult hippocampus of wild type mice in either control conditions (injection of saline) of after injection of kainic acid (synaptic stimulation). Coronal cryosections were hybridized with radio-labelled oligonucleotides specific for RbAp48. Expression of RbAp48 is upregulated specifically in the dentate gyrus (DG) eight hours after the application of kainic acid. This upregulation of RbAp48 lasted for four hours (8 hr to 12 hr time points).

DETAILED DESCRIPTION OF THE INVENTION

Terms

As used in this application, except as otherwise expressly provided herein, each of the following terms shall have the meaning set forth below.

As used herein, "administering" an agent can be effected or performed using any of the various methods and delivery systems known to those skilled in the art. The administering can be performed, for example, intravenously, via cerebrospinal fluid, orally, nasally, via implant, transmucosally, transdermally, intramuscularly, and subcutaneously.

As used herein, "agent" shall mean any chemical entity, including, without limitation, a protein, an antibody, a nucleic acid, a small molecule, and any combination thereof. In one embodiment, the agent is known to cross the blood/brain barrier of a mammal (e.g. a human).

As used herein, "nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

As used herein, "pharmaceutically acceptable carrier" shall mean any of the various carriers known to those skilled in the art.

The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and anti-oxidants (e.g., parabens, vitamins E and C, and ascorbic acid), anti-caking agents, coating agents, and chelating agents (e.g., EDTA).

As used herein, "subject" shall mean any animal, such as a primate (e.g. monkey), mouse, rat, guinea pig or rabbit. In the preferred embodiment, the subject is a human.

As used herein, "therapeutically effective amount" means an amount sufficient to treat a subject afflicted with a disorder or a complication associated with a disorder. The therapeutically effective amount will vary with the subject being treated, the condition to be treated, the agent delivered and the route of delivery. A person of ordinary skill in the art can perform routine titration experiments to determine such an amount. Depending upon the agent delivered, the therapeutically effective amount of agent can be delivered continuously, such as by continuous pump, or at periodic intervals (for example, on one or more separate occasions). Desired time intervals of multiple amounts of a particular agent can be determined without undue experimentation by one skilled in the art. In one embodiment, the therapeutically effective amount is from about 1 mg of agent/subject to about 1 g of agent/subject per dosing. In another embodiment, the therapeutically effective amount is from about 10 mg of agent/subject to 500 mg of agent/subject. In a further embodiment, the therapeutically effective amount is from about mg of agent/subject to 200 mg of agent/subject. In a further embodiment, the therapeutically effective amount is about 100 mg of agent/subject. In still a further embodiment, the therapeutically effective amount is selected from 50 mg of agent/subject, 100 mg of agent/subject, 150 mg of agent/subject, 200 mg of agent/subject, 250 mg of agent/subject, 300 mg of agent/subject, 400 mg of agent/subject and 500 mg of agent/subject. Depending upon the agent delivered, the therapeutically effective amount of agent can be delivered continuously, such as by continuous pump, or at periodic intervals (for example, on one or more separate occasions). Desired time intervals of multiple amounts of a particular agent can be determined without undue experimentation by one skilled in the art.

As used herein, "treating" a disorder shall mean slowing, stopping or reversing the disorder's progression.

RbAp48 (also known as retinoblastoma binding protein 4 (RBBP4) encodes a ubiquitously expressed nuclear protein which belongs to a high conserved subfamily of WD-repeat proteins. It is present in protein complexes involved in histone acetylation and chromatin assembly. Three transcriptional variants have been reported for RbAp48. Isoform a is the longest isoform and has been chosen as the canonical sequence. The amino acid sequence of isoform a of RbAp48 is as follows:

```
                                                (SEQ ID NO: 1)
MADKEAAFDD AVEERVINEE YKIWKKNTPF LYDLVMTHAL

EWPSLTAQWL PDVTRPEGKD FSIHRLVLGT HTSDEQNHLV

IASVQLPNDD AQFDASHYDS EKGEFGGFGS VSGKIEIEIK

INHEGEVNRA RYMPQNPCII ATKTPSSDVL VFDYTKHPSK

PDPSGECNPD LRLRGHQKEG YGLSWNPNLS GHLLSASDDH

TICLWDISAV PKEGKVVDAK TIFTGHTAVV EDVSWHLLHE

SLFGSVADDQ KLMIWDTRSN NTSKPSHSVD AHTAEVNCLS

FNPYSEFILA TGSADKTVAL WDLRNLKLKL HSFESHKDEI

FQVQWSPHNE TILASSGTDR RLNVWDLSKI GEEQSPEDAE

DGPPELLFIH GGHTAKISDF SWNPNEPWVI CSVSEDNIMQ

VWQMAENIYN DEDPEGSVDP EGQGS
```

Embodiments of the Invention:

This invention provides a transgenic mouse comprising two transgenes, each of which transgene comprises a DNA sequence encoding a dominant negative form of RbAp48 protein, wherein the expression of the dominant negative form of RbAp48 is spatially restricted to the forebrain by a CaM Kinase IIa promoter and wherein the expression of the dominant negative form of RbAp48 is controlled by tetracycline-controlled transcriptional activation.

In an embodiment, the transgenes are integrated in the genomic DNA.

In an embodiment, the DNA sequence encoding a dominant negative form of RbAp48 encodes an RbAp48 protein lacking the N-terminal 54 amino acids of RbAp48.

In an embodiment, the expression of the dominant negative form of RbAp48 is activated at any day post birth. For example, the expression of the dominant negative form of RbAp48 is activated at day p1, p2, p3, p4, p5, p6, p7, p8, p9, p10, p11, p12, p13, p14, p15, p16, p17, p18, p19, p20, p21, p22, p23, p24, p25, p26, p27, p28, p29, p30, p31, p32, p33, p34, p35, p36, p37, p38, p39, p40, p41, p42, p43, p44, p45, p46, p47, p48, p49, p50, p51, p52, p53, p54, p55, p56 and so forth. In an embodiment, the expression of the dominant negative form of RbAp48 is activated at day p40.

In an embodiment, the expression of the dominant negative form of RbAp48 is activated by feeding the transgenic mouse doxycycline-free food. In another embodiment, the expression of the dominant negative form of RbAp48 is activated by feeding the transgenic mouse doxycycline-free food.

In an embodiment, the expression of the dominant negative form of RbAp48 results in a decrease of relative cerebral blood volume of the dentate gyrus as compared to the relative cerebral blood volume of the dentate gyrus in the transgenic mouse when the dominant negative form of RbAp48 is not expressed. In another embodiment, the expression of the dominant negative form of RbAp48 in the transgenic mouse results in lower relative cerebral blood volume of the dentate gyrus of the transgenic mouse as compared to a transgenic mouse of the same age which is not expressing the dominant negative form of RbAp48.

In an embodiment, the expression of the dominant negative form of RbAp48 reduces the amount of acetylation of histones in the dentate gyrus of the transgenic mouse as compared to the amount of acetylation of histones in the dentate gyrus when the dominant negative form of RbAp48 is not expressed. In an embodiment, the expression of the dominant negative form of RbAp48 reduces the amount of acetylation of histones H4 and H2B in the dentate gyrus of the transgenic mouse as compared to the amount of acetylation of histones H4 and H2B in the dentate gyrus when the dominant negative form of RbAp48 is not expressed.

In an embodiment, the expression of the dominant negative form of RbAp48 reduces memory function of the transgenic mouse as compared to the memory function of the transgenic mouse when the dominant negative form of RbAp48 is not expressed.

Provided herein is a method for evaluating in a transgenic mouse the potential therapeutic effect of an agent for slowing, inhibiting or preventing age-related memory decline in a mammalian subject, which method comprises: (a) administering the agent to the transgenic mouse described hereinabove, wherein expression of the dominant negative form of RbAp48 is activated prior to administering the agent to the transgenic mouse; and (b) determining, after a suitable period of time, the memory function of the transgenic mouse of step (a), wherein an increase in the memory function determined in step (b) as compared to the memory function determined in a transgenic mouse described hereinabove expressing the dominant negative form of RbAp48 to which the agent has not been administered indicated that the agent has a potential therapeutic effect for slowing, inhibiting or preventing age-related memory decline in the mammalian subject.

In an embodiment, the agent increases RbAp48 expression. In an embodiment the agent is epicatechin.

In an embodiment, the agent is a histone acetyl transferase. In an embodiment, the histone acetyl transferase is selected from the group consisting of CREBBP, CDY1, CDY2, CDYL1, CLOCK, ELP3, EP300, HAT1, KAT2A, KAT2B, KAT5, MYST1, MYST2, MYST3, MYST4, NCOA1, NCOA3, NCOAT, and TF3C4.

In an embodiment, the agent is a histone deactylase (HDAC) inhibitor. In an embodiment, the HDAC inhibitor is selected from the group consisting of belinostat, mocetinostat, panobinostat, dacinostat, 4-Dimethylamino-N-(6-hydroxycarbamoylhexyl)-beinzamide, N-(2-aminophenyl)-N'-phenyl-octanediamide, etinostat, tacedinaline, suberoylanilide hydroxamic acid (SAHA), trichostatin A, traproxin B, valproic acid, (E)-3-(2-butyl-1-(2-(diethylamino) ethyl)-1H-benzo[d]imidazol-5-yl)-N-hydroxyacrylamide, romidepsin, givinostat, and sulforaphane.

In an embodiment, the agent is a phosphodiesterase (PDE) inhibitor. In an embodiment, the phosphodiesterase inhibitor is selected from the group consisting of an inhibitor of PDE1, an inhibitor of PDE2, an inhibitor of PDE3, an inhibitor of PDE4, an inhibitor of PDE5, an inhibitor of PDE6, an inhibitor of PDE7, and inhibitor of PDE9 and an inhibitor of PDE10. In an embodiment the phosphodiesterase inhibitor is selected from the group consisting of vinpocetine, erythro-9-(2-hydroxy-3-nonyl)adenine), arofyllin, denbufylline, Drotaverine, etazolate, filaminast, (3R,5R)-5-(3-(cyclopentyloxy)-4-methoxyphenyl)-3-(3-methylbenzyl)piperidin-2-one, ibudilast, irsogladine, mesembrine, roflumilast, rolipram, MEM 1917 (available from Memory Pharmaceuticals, Montvale N.J.) and MEM 1414 (available from Memory Pharmaceuticals, Montvale, N.J.). MEM 1917 and MEM 1414 are inhibitors of phosphodiesterase 4 (PDE4).

Inhibitors of PDE4 are described, for example, in U.S. Pat. Nos. 7,723,348; 7,700,631; 7,696,198; 7,655,802; 7,585,882; 7,495,017; 7,432,266; 7,405,230; 7,342,021; 7,335,654; 7,332,486; 7,235,579; 7,205,320; 7,153,871; 7,087,625; and 6,699,890, the entire contents of each of which are hereby incorporated by reference. In an embodiment, the agent may be any one of the PDE4 inhibitors described herein.

Inhibitors of PDE5 include for ezample, but are not limited to, Acetildenafil, Aildenafil, Avanafil, Dipyridamole, Icariin, lodenafil, mirodenafil, sildenafil, fuldoaildenafil, tadalafil, udenafil and vardenafil. In an embodiment, the agent may be any one of the PDE5 inhibitors described herein. PDE6 inhibitors include, for example, but are not limited to Zaprinast. In an embodiment, the agent may be any one of the PDE6 inhibitors described herein. PDE10 inhibitors include, but are not limited to Papaverine and tofisopam. In an embodiment, the agent may be any one of the PDE10 inhibitors described herein.

In an embodiment of the above method, the memory function is tested using novel object recognition. In an embodiment of the above method, the memory function is tested by testing spatial memory task using the Morris water maze. In an embodiment of the above method, the expression of the dominant negative form of RbAp48 in the transgenic mouse of step (a) is activated at day p40.

This invention provides a method for evaluating in a transgenic mouse the potential therapeutic effect of an agent for slowing, inhibiting or preventing age-related memory decline in a mammalian subject, which method comprises: (a) administering the agent to the transgenic mouse of claim 1, wherein expression of the dominant negative form of RbAp48 is activated prior to administering the agent to the transgenic mouse; and (b) measuring, after a suitable period of time, the cerebral blood volume (cbv) in the dentate gyrus of the transgenic mice of step (a); wherein an increase in cbv measured in step (b) as compared to the cbv measured in a transgenic mouse of claim 1 expressing the dominant negative form of RbAp48 to which the agent has not been administered indicates that the agent has a potential therapeutic effect for slowing, inhibiting or preventing age-related memory decline in the mammalian subject.

In an embodiment, the agent increases RbAp48 expression. In an embodiment the agent is epicatechin.

In an embodiment, the agent is a histone acetyl transferase. In an embodiment, the histone acetyl transferase is selected from the group consisting of CREBBP, CDY1, CDY2, CDYL1, CLOCK, ELP3, EP300, HAT1, KAT2A, KAT2B, KAT5, MYST1, MYST2, MYST3, MYST4, NCOA1, NCOA3, NCOAT, and TF3C4.

In an embodiment, the agent is a histone deactylase (HDAC) inhibitor. In an embodiment, the HDAC inhibitor is selected from the group consisting of belinostat, mocetinostat, panobinostat, dacinostat, 4-Dimethylamino-N-(6-hydroxycarbamoylhexyl)-beinzamide, N-(2-aminophenyl)-N'-phenyl-octanediamide, etinostat, tacedinaline, suberoylanilide hydroxamic acid (SAHA), trichostatin A, traproxin B, valproic acid, (E)-3-(2-butyl-1-(2-(diethylamino) ethyl)-1H-benzo[d]imidazol-5-yl)-N-hydroxyacrylamide, romidepsin, givinostat, and sulforaphane.

In an embodiment, the agent is a phosphodiesterase (PDE) inhibitor. In an embodiment, the phosphodiesterase inhibitor is selected from the group consisting of an inhibitor of PDE1, an inhibitor of PDE2, an inhibitor of PDE3, an inhibitor of PDE4, an inhibitor of PDE5, an inhibitor of PDE6, an inhibitor of PDE7, and inhibitor of PDE9 and an inhibitor of PDE10. In an embodiment the phosphodiesterase inhibitor is selected from the group consisting of vinpocetine, erythro-9-(2-hydroxy-3-nonyl)adenine), arofyllin, denbufylline, Drotaverine, etazolate, filaminast, (3R,5R)-5-(3-(cyclopentyloxy)-4-methoxyphenyl)-3-(3-methylbenzyl)piperidin-2-one, ibudilast, irsogladine, mesembrine, roflumilast, rolipram, MEM 1917 (available from Memory Pharmaceuticals, Montvale N.J.) and MEM 1414 (available from Memory Pharmaceuticals, Montvale, N.J.). MEM 1917 and MEM 1414 are inhibitors of phosphodiesterase 4 (PDE4).

Inhibitors of PDE4 are described, for example, in U.S. Pat. Nos. 7,723,348; 7,700,631; 7,696,198; 7,655,802; 7,585,882; 7,495,017; 7,432,266; 7,405,230; 7,342,021; 7,335,654; 7,332,486; 7,235,579; 7,205,320; 7,153,871; 7,087,625; and 6,699,890, the entire contents of each of which are hereby incorporated by reference. In an embodiment, the agent may be any one of the PDE4 inhibitors described herein.

Inhibitors of PDE5 include for example, but are not limited to, Acetildenafil, Aildenafil, Avanafil, Dipyridamole, Icariin, lodenafil, mirodenafil, sildenafil, fuldoaildenafil, tadalafil, udenafil and vardenafil. In an embodiment, the agent may be any one of the PDE5 inhibitors described herein. PDE6 inhibitors include, for example, but are not limited to Zaprinast. In an embodiment, the agent may be any one of the PDE6 inhibitors described herein. PDE10 inhibitors include, but are not limited to Papaverine and tofisopam. In an embodiment, the agent may be any one of the PDE10 inhibitors described herein.

In an embodiment, the expression of the dominant negative form of RbAp48 of the transgenic mouse of step (a) is activated at day p40.

This invention provides A method for treating a subject afflicted with age-related memory decline comprising administering to the subject a therapeutically effective amount of an agent which increases the expression of RbAp48 protein in the cells of the subject's brain, wherein the agent is selected from the group consisting of epicatechin.

This invention also provides a method for treating a subject afflicted with age-related memory decline comprising administering to the subject a therapeutically effective amount of an agent which inhibits the deactylation of histones in the dentate gyrus of the subject, thereby treating the subject afflicted with the age-related memory decline.

In an embodiment, the agent is a histone deactylase (HDAC) inhibitor. In an embodiment, the HDAC inhibitor is selected from the group consisting of belinostat, mocetinostat, panobinostat, dacinostat, 4-Dimethylamino-N-(6-hydroxycarbamoylhexyl)-beinzamide, N-(2-aminophenyl)-N'-phenyl-octanediamide, etinostat, tacedinaline, suberoylanilide hydroxamic acid (SAHA), trichostatin A, traproxin B, valproic acid, (E)-3-(2-butyl-1-(2-(diethylamino)ethyl)-1H-benzo[d]imidazol-5-yl)-N-hydroxyacrylamide, romidepsin, givinostat, and sulforaphane.

In an embodiment, the agent inhibits the deactylation of histone H4. In an embodiment, the agent inhibits the deactylation of histone H2B. In an embodiment, the agent inhibits the deactylation of histones H4 and H2B.

This invention provides a method for treating a subject afflicted with age-related memory decline comprising administering to the subject a therapeutically effective amount of an agent which increase the acetylation of histones in the dentate gyrus of the subject, thereby treating the subject afflicted with the age-related memory decline.

In an embodiment, the agent is a histone acetyltransferase. In an embodiment, the agent inhibits the deactylation of histone H4. In an embodiment, the agent inhibits the deactyla-tion of histone H2B. In an embodiment, the agent inhibits the deactylation of histones H4 and H2B.

This invention is illustrated in the Experimental Details section which follows. This section is set forth to aid in an understanding of the invention but is not intended to, and should not be construed to limit in any way the invention as set forth in the claims which follow thereafter.

Experimental Details

Synopsis

The molecular defects contributing to age-related hippocampal dysfunction in humans remain unknown. Here this issue is addressed by focusing on a spatiotemporal pattern of hippocampal dysfunction that thought to distinguishes cognitive aging in humans from Alzheimer's disease. Using microarray analysis gene-expression levels of the human dentate gyrus (DG) and the entorhinal cortex are profiled, the hippocampal subregions thought to be differentially affected and resistant to aging. A deficiency in RbAp48, a histone binding protein that modifies histone acetylation, was identified and this finding was then confirmed by protein analysis. To test for a causal role in cognitive aging, a transgenic mouse was generated that expressed a dominant-negative inhibitor of RbAp48 in a temporally regulated fashion in the adult forebrain. Inhibiting RbAp48 at a relatively young age was found to cause hippocampal-dependent memory deficits observed in aging. Furthermore, by using functional magnetic resonance imaging (fMRI), inhibition of RbAp48 phenocopied the spatial pattern of hippocampal dysfunction described in aging, and corresponds to an observed decrease in histone acetylation. In addition to linking human RbAp48 deficiency to aging and hippocampal dysfunction, these findings establish the importance of chromatin acetylation as a molecular pathway contributing to cognitive aging.

Methods

Gene-Expression Profiling: Eight brains, free of Alzheimer's disease and other histopathology, were obtained at autopsy under a protocol approved by the institution's review board. The dentate gyrus and the entorhinal cortex were identified and sectioned using strict anatomical criteria, following New York Brain Bank procedures. Samples were snap frozen in liquid nitrogen and stored at −80° C. For each of the 16 brain samples, total RNA was extracted from entorhinal cortex and dentate gyrus with TRIzol (Invitrogen) and purified with RNeasy column (Invitrogen). 10 μg total RNA were used to prepare double-stranded cDNA (Superscript, Invitrogen). The T7-(dT)$_{24}$ primer for cDNA synthesis contained a T7 RNA polymerase promoter site. In vitro transcription with biotin-labeled ribonucleotides was performed on the cDNA to produce cRNA probes (Bioarray High Yield RNA Transcript Labeling Kit, ENZO Life Sciences). HG-U133A microarrays (Affymetrix) were hybridized with fragmented cRNA for 16 h at 45° C. with constant rotation (60 g). Microarrays were washed and stained on a fluidics station, and scanned using a confocal microscope. HG-U133A microarrays were analyzed with Affymetrix Microarray Suite v5.0 and GeneSpring v5.0.3 (Silicon Genetics) software, and scaled to a value of 500. Samples with a 3'/5' ratio of control genes actin and GAPDH greater than 7 were excluded from analysis. Transcripts whose detection levels had a p-value greater than 0.05 were excluded, and raw data of the 6566 included transcripts are provided Generation of Transgenic Mice The mouse RbAp48 open reading frame lacking the region encoding the first 54 N-terminal aminoacids was amplified by PCR and fused to the Flag tag epitope and subsequently cloned into a modified pMM400 plasmid[37] (for oligonucleotides see supplemental table 3). The generation of the mice and the tetO-driven gene expression have been described previously[37].

Maintenance of Mice and Genetic Background Mice were maintained and bred under standard conditions, consistent with NIH guidelines and approved by the Institutional Animal Care and Use Committee. To control genetic background, we followed the recommendations made by the Banbury conference[37,38] The tetO-RbAp48-DN-Flag mice were backcrossed at least six times to C57B1/6J background and bred with CaMKII-tTA mice that were backcrossed 16 to 18 times to the 129SveVTac background.

RNA In Situ Hybridizations: RNA in situ hybridizations were performed on fresh frozen adult brain slices using 40-45 base anti-sense oligonucleotides[37]. The oligonucleotides used for the detection of RbAp48-DN-Flag and RbAp48 transcripts can be found in supplemental table 3.

Western Blotting Mouse hippocampi were homogenized in 50 mM Tris-HCl pH 7.4 and 2% SDS buffer with protease inhibitors (Roche). 10-20 μg of homogenates were separated by SDS-PAGE and transferred to PVDF membranes (Bio-Rad). Membranes were blocked in 5% milk in TBS and 0.1% tween 20. Horseradish peroxidase-conjugated secondary antibodies were from Jackson Immunoresearch. Anti-RbAp48 antibody (rabbit) was from Genetex. Anti-Flag M2 antibody (mouse) was from Sigma.

Human brain samples were homogenized in 20 mM Tris HCl pH 7.9, 150 mM NaCl, 5% NP-40, 1 mM EDTA, 10 mM ABESF, and protease inhibitors. 40 μg of total protein were used for western blots. Membranes were blocked in Super-Block Blocking Buffer in TBS and 0.1% Tween 20 (Thermo Scientific). Anti-RbAp48 antibody was from Thermo Scientific. Temperature and time conditions were as above.

Reverse Transcription Polymerase Chain Reaction Total RNA from adult mouse hippocampi was extracted as suggested by the manufacturer (GIBCO BRL). 250 ng of DNase I-treated total RNA were applied to Reverse Transcription using random hexamers and following the manufacturer's instructions (Invitrogen). To isolate and clone the mouse RbAp48 cDNA, we used the following primers: Forward: 5'-TCCTGCAACGCACGACCC-3' (SEQ ID NO:2) and Reverse: 5'-CAAAGTCTGTGCCTCAAACC-3'. (SEQ ID NO:3)

Immunohistochemistry Three month old mice were anesthetized and perfused intracardiacally with 50 ml of ice cold 4% paraformaldehyde in 0.1M $Na_2HPO_4/NaH_2PO_4$ pH 7.4 buffer. The brains were post-fixed overnight at 4° C. and coronal sections (30 μm of thickness) were taken using a vibratome (Vibratome). The staining method has been described previously[39].

Behavior The experimenter was "blind" to the genotype. The CaMKIIα-tTa, tetO-RbAp48-DN-Flag single transgenic and wild type mice (no transgene in the genome) performed equally and were pooled together in the control group.

Elevated Plus-Maze It was performed as previously described[40]. The data were statistically evaluated using ANOVA, with the genotype as the between factor and the arm (open and enclosed) as the within factor.

Open Field Activity was recorded for 60 min. ANOVAs with the genotype as the between factor and the zone (center or periphery) as the within factor were used for the statistical analysis.

Water Maze The task was performed as previously described[40]. Statistical analyses used ANOVAs with genotype as the between-subject factor and day and area (quadrant or platform during the probe trials) as within-subject factors. Scheffe's test was used for post-hoc analysis.

Novel Object Recognition Task It has been described previously[41]. The discrimination index was determined by the difference in exploration time expressed as a ratio of the total time spent exploring the two objects.

fMRI: The details of how cerebral blood volume (CBV) maps of the mouse hippocampal formation were generated has been previously described[9] Briefly, a 9.4 Tesla scanner (Bruker, AVANCBV 400WB) was used to acquire axial T2-weighted images (TR/TE=2000 ms/70 ms; FOV=19.6 mm; acquisition matrix=256×256; slices; slice thickness=0.6 mm), perpendicular to the hippocampal long axis, before and 45-minutes after IP administration of gadolinium-pentate (Omniscan, 013 mmol/kg). Isofluorane was chosen as the anesthetic agent because of its minimal effects on hemodynamic coupling, and heart rate, respiratory rate, and SaO2 were monitored throughout. Relative CBV maps were generated according to formula CBV LR2=ln (Spre/Spost)/TE; where TE=effective echo-time; Spre=signal before contrast; Spost=signal contrast agent reaches steady-state. The derived image was then divided by the maximum 4 pixels signal value of the posterior cerebral vein to control for differences in levels of contrast yielding relative CBV.

Histone Acetylation Assays Immunohistochemistry on floating brain sections from adult mice (3 months) was performed. The Metamorph software was used for image quantification. Antibodies against acetylated histones H2B (lys20), H3 (lys9) and H4 (lys12) were from Cell Signaling. The number and genotypes of mice used are described in supplemental table 2.

Treatment with Kainic Acid Kainic acid (Sigma) was injected intraperitoneally as previously described[42]

Results & Discussion

Isolated here are mechanisms linked to hippocampal dysfunction associated not with AD but with age-related memory decline. Guided by the spatiotemporal pattern that is thought to distinguish age-related hippocampal dysfunction from Alzheimer's disease, the DG was harvested from healthy human brains ranging from 33 to 88 years of age. Additionally, the EC was harvested from each brain as a within-brain control. Gene-expression profiles of each individual tissue sample was generated using affymetrix microarray chips. DG expression levels were first normalized against the EC, and the normalized DG transcripts were then correlated against age. Nineteen transcripts were identified that linearly increased or decreased with age, with a p-value<0.005. Among these genes, the gene whose expression levels best conformed to the spatiotemporal pattern of normal aging was RbAp48 (beta=−0.97, p=0.005).

Figure 3:
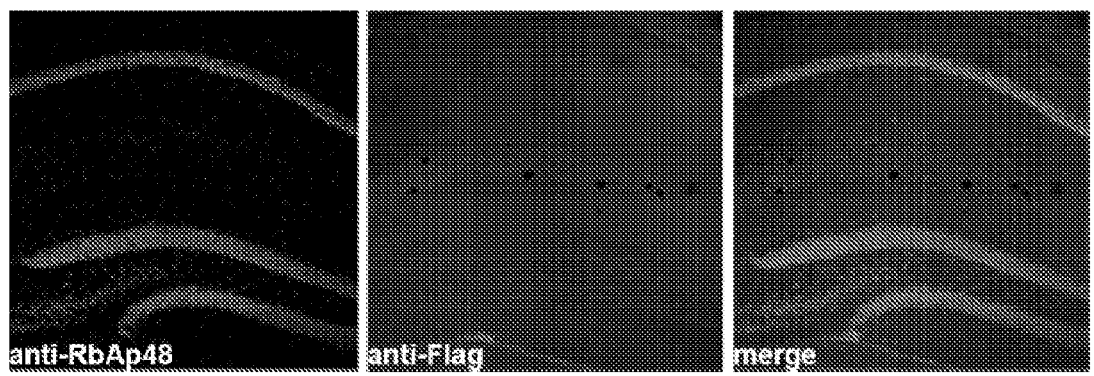
FIG. 3: Control immunostaining of hippocampus from adult single-tetO-RbAp48-DN mouse using anti-Flag and anti-RbAp48 antibodies. The anti-Flag antibody recognizes the recombinant RbAp48-DN protein and therefore no immunostaining is detected (compare with FIG. 2d).

This finding was replicated and extended by completing a protein level analysis. The EC and DG were harvested, as well as additional hippocampal subregions—the CA3, CA1, and subiculum—from separate group of 10 healthy human brains, ranging from 41 to 89 years of age. Western blots were used to measure RbAp48 and actin levels from each tissue sample. In a primary analysis, an age-related change was tested in the DG and EC. RbAp48 protein level was found to decline in the DG (beta=−0.72, p=0.02), but not the EC (beta=0.13, p=0.71) (FIG. 1). In a secondary analysis, RbAp48 protein levels were not found to significantly decline with age in other subregions (CA3: beta=0.09, p=0.81; CA1: beta=−0.48, p=0.16; subiculum: beta=0.12, p=0.62). RbAp48 plays a role in histone acetylation a pathway implicated in normal hippocampal function and aging[16-21]. To establish a causal role of RbAp48 in the pathogenesis of age-related memory decline, the role of RbAp48 in the adult mouse forebrain was studied and the effect of inhibiting the function of RbAp48 in the hippocampus was examined, a brain area where RbAp48 is expressed (FIG. 2a). A mouse line was generated which expressed a dominant negative form of RbAp48 (henceforth RbAp48-DN). This form of RbAp48 lacks its first 54 N-terminal amino acid residues, critical for the interaction of RbAp48 with histone H4, but retains its ability to bind to histone modification factors through its WD40 repeats[22]. The expression of the RbAp48-DN was controlled spatially to the forebrain by the CaM Kinase IIa promoter, and temporally with the tTA system[23] (FIG. 2b). The advantage of this approach is that it allows the inhibition of RbAp48 function in the adult forebrain of tetO-RbAp48-DN/CaMKIIa-tTA double-transgenic mice in a spatially restricted and reversible manner (FIG. 2b). To discriminate between the endogenous and the recombinant RbAp48 proteins, a Flag epitope tag was fused at the N-terminus of RbAp48-DN. Western blot analysis confirmed the expression of the RbAp48-DN protein in the adult hippocampus of the double-transgenic mice (FIG. 2c). Immunostainings of adult brain slices from double-transgenic mice for RbAp48 and RbAp48-DN using antibodies specific for RbAp48 and the Flag epitope showed that both proteins were expressed in the same neurons and displayed similar (nuclear) localization (FIG. 2d and FIG. 3). To avoid any developmental effect, the transcription of the RbAp48-DN transgene in the double-transgenic mice was activated at day P40 (FIG. 2b).

Figure 7:
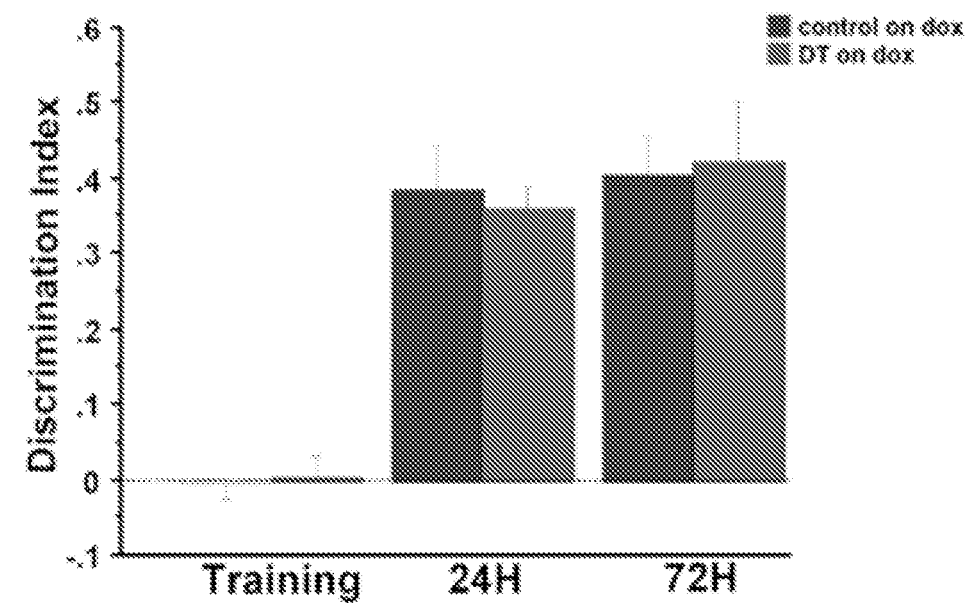
FIG. 7: Data from novel object recognition task of animals that were kept on dox during the task The mean discrimination index and total exploration time±SEM are shown. The double-transgenic mice on dox (DT on dox) and control on dox animals displayed similar total exploration times and discrimination indexes in both sessions of the task (repeated-measures ANOVA did not reveal genotype or genotype*session effects; exploration time: $F_{(1,25)}=0.05$, $p=0.8244$ & $F_{(2,50)}=0.093$, $p=0.9111$; discrimination index: $F_{(1,25)}=0.001$, $p=0.9913$ & $F_{(2,50)}=0.106$, $p=0.8994$; genotype & genotype*session effects, respectively).
Figure 7:
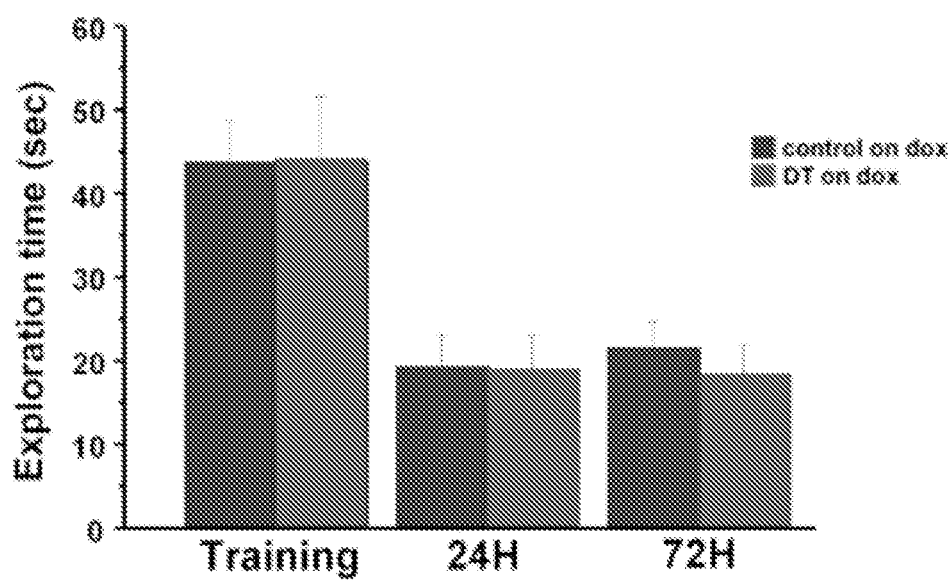

It was next examined whether inhibiting the function of RbAp48 in the adult forebrain interferes with memory. The mice were first characterized behaviourally. Because differences in anxiety can affect cognitive performance this possibility was excluded by showing that all groups perform equivalently on the elevated plus maze and open field (FIG. 4). To test for hippocampal-dependent dysfunction the novel object recognition task was used. Unlike other rodent tasks, variants of novel objection recognition task can be used across mammalian species and indeed an age-related decline in object recognition has been documented in humans[24-26] as well as animal models[27-29]. Adult mice (3½ months) were placed in an open arena containing two identical novel objects and they were allowed to explore them for 15 minutes[31]. The total exploration time was similar among all groups of animals and the mice independent of genotype explored both objects equally (FIG. 5a). Twenty-four hours after the training session, the animals were placed back in the arena where one familiar and one novel object were presented. Control and double-transgenic mice displayed similar performance and a large preference for the novel object, indicating robust memory for the familiar object (FIG. 5a). Strikingly, after two days the control mice still explored the novel object while the double-transgenic mice did not show any preference for this object (FIG. 5a). The tTA system allowed for examination of whether the memory deficit in the double-transgenic mice results from acute action of the RbAp48-DN protein and whether it would be reversed by blockade of RbAp48 function in mature adult forebrain neurons, or from an early effect of its expression between the day of its activation (day P40) and adulthood or position effects of the transgenes. The double-transgenic animals and their control littermates remained on doxycycline-containing food until day P40, at which point they were switched to doxycycline-free food. At day P80, the mice shifted back to doxycycline-containing food and the expression of RbAp48-DN was blocked. The mice were then tested in the novel object recognition task when they were 3½ months old after assuring that there were no differences in anxiety between genotypes (FIG. 6). It was found that double-transgenic and control mice on dox displayed similar performance (FIG. 7). Together, these data indicate that inhibition of RbAp48 function in the forebrain of relatively young adult mice recapitulates behavioural defects characteristic of cognitive aging.

Next, the performance of the mice in a spatial memory task in the Morris water maze[30] was examined. Although this task can be normally performed with relatively subtle molecular defects in the DG, selective lesions to the DG cause impairments in this task. The double-transgenic mice learned the task similar to their control siblings (FIG. 8), but they had impaired memory as evidenced by a significant decrease in platform-location crossings during a probe trial one day after the end of acquisition (FIG. 5b). Comparison of non-cognitive parameters revealed no differences between the groups (FIG. 9), suggesting that the observed behavioral defects resulted from impaired hippocampal-dependent spatial memory and not from changes in motor or motivational processes. The mice were also tested for their ability to use the acquired spatial configuration and learn a new platform location. Again, the double-transgenic mice were impaired in forming a memory of the new platform location as they explored the new training quadrant and crossed the platform location significantly less often than the control animals in a probe trial one day after the end of training (FIG. 5c & FIG. 8). Double-transgenic and control animals on dox were also tested but there was no observed differences in these animals (FIGS. 10 and 11).

If RbAp48 deficiency underlies age-related hippocampal dysfunction, inhibiting RbAp48 in relatively young adult mice (3½ months) should also recapitulate the DG-preferential dysfunction observed by fMRI[8-10]. To explore this idea, a variant of fMRI was used that maps regional cerebral blood volume (CBV), a hemodynamic correlate of metabolism that generates functional maps with high spatial resolution[31,32] and which has proven well-suited for pinpointing hippocampal dysfunction in mouse models[9,33-35]. Compared to control mice (n=18), RbAp48-DN expression (n=9) caused differential dysfunction in the DG ($F=6.3$, $p=0.019$) (FIGS. 12a & 12b). This dysfunction was specific to the expression of the RbAp48-DN as it was reversed when the expression of RbAp48-DN was turned off in the adult forebrain (FIGS. 12a & 12b).

Because RbAp48 regulates histone acetylation, it was explored whether RbAp48-DN affects the steady state levels of histone acetylation in the hippocampal formation using immunohistochemistry and image quantification analysis to measure histone acetylation. The initial focus was on the DG. By comparing the DG of RbAp48-DN mice to controls, it was found that inhibition of RbAp48 caused a selective reduction in acetylation of histones H4 and H2B (FIGS. 12c & 12d and FIG. 13). To test for spatial specificity, the CA1 subregion was examined and no significant reduction in histone acetylation (FIGS. 12c & 12d) was found. As with behavior and fMRI, the effect of RbAp48-DN on H2B and H4 acetylation in the adult DG was reversed when its expression was turned off (mice on dox; FIGS. 12c & 12d). The observed DG effects of RbAp48-DN expression, and consequently inhibition of RbAp48 function, suggest that Rbap48 plays an important role in DG-dependent molecular processes underlying memory function. In support of this idea, RbAp48 expression is differentially upregulated in the DG in response to synaptic stimulation (FIG. 14).

In summary, an age-related deficiency of RbAp48 was isolated in the aging human hippocampal formation and transgenic mice were used to validate this finding. The observation that inhibition of RbAp48 in the forebrain of relatively young mice recapitulates the behavioral and fMRI profiles of cognitive aging supports the interpretation that age-related RbAp48 deficiency in the DG plays a causal role in human hippocampal dysfunction. Besides providing a histological correlate of the fMRI findings, the observed decrease in histone H2B acetylation is interesting as previous studies have shown that a deficiency in CREB-binding protein (CBP) also causes a decrease in H2B acetylation and mediates hippocampal dysfunction[16]. Moreover, RbAp48 interacts with CBP and thereby regulates its HAT activity[36]. Beyond the specific role played by RbAp48, therefore, our results are the first to link defects in histone acetylation in the DG to human age-related hippocampal dysfunction.

REFERENCES

1. Small, S. A. Age-related memory decline; current concepts and future directions. *Archives of Neurology* 58, 360-364 (2001).
2. Lein, E. S., et al. Genome-wide atlas of gene expression in the adult mouse brain. *Nature* 445, 168-176 (2007).
3. Braak, H., Alafuzoff, I., Arzberger, T., Kretzschmar, H. & Del Tredici, K. Staging of Alzheimer disease-associated neurofibrillary pathology using paraffin sections and immunocytochemistry. *Acta Neuropathol* 112, 389-404 (2006).
4. Thal, D. R., Rub, U., Orantes, M. & Braak, H. Phases of A beta-deposition in the human brain and its relevance for the development of AD. *Neurology* 58, 1791-1800 (2002).
5. Gomez-Isla, T., et al. Profound loss of layer II entorhinal cortex neurons occurs in very mild Alzheimer's disease. *J Neurosci* 16, 4491-4500 (1996).
6. West, M. J. Regionally specific loss of neurons in the aging human hippocampus. *Neurobiol Aging* 14, 287-293 (1993).
7. Small, S. A., Perera, G. M., DeLaPaz, R., Mayeux, R. & Stern, Y. Differential regional dysfunction of the hippocampal formation among elderly with memory decline and Alzheimer's disease. *Ann Neurol* 45, 466-472 (1999).
8. Small, S. A., Tsai, W. Y., DeLaPaz, R., Mayeux, R. & Stern, Y. Imaging hippocampal function across the human life span: is memory decline normal or not? *Ann Neurol* 51, 290-295 (2002).
9. Moreno, H., et al. Imaging the abeta-related neurotoxicity of Alzheimer disease. *Arch Neurol* 64, 1467-1477 (2007).
10. Small, S. A., Chawla, M. K., Buonocore, M., Rapp, P. R. & Barnes, C. A. From The Cover: Imaging correlates of brain function in monkeys and rats isolates a hippocampal subregion differentially vulnerable to aging. *Proc Natl Acad Sci USA* 101, 7181-7186 (2004).
11. Toner, C. K., Pirogovsky, E., Kirwan, C. B. & Gilbert, P. E. Visual object pattern separation deficits in nondemented older adults. *Learn Mem* 16, 338-342 (2009).
12. Yassa, M. A., et al. Pattern separation deficits associated with increased hippocampal CA3 and dentate gyrus activity in nondemented older adults. *Hippocampus* (2010).
13. Stark, S. M., Yassa, M. A. & Stark, C. E. Individual differences in spatial pattern separation performance associated with healthy aging in humans. *Learn Mem* 17, 284-288 (2010).
14. Brickman, A. M., Stern, Y. & Small, S. A. Hippocampal subregions differentially associate with standardized memory tests. *Hippocampus* (2010).
15. Albert, M. S. The ageing brain: normal and abnormal memory. *Philos Trans R Soc Lond B Biol Sci* 352, 1703-1709 (1997).
16. Alarcon, J. M., et al. Chromatin acetylation, memory, and LTP are impaired in CBP+/− mice: a model for the cognitive deficit in Rubinstein-Taybi syndrome and its amelioration. *Neuron* 42, 947-959 (2004).
17. Korzus, E., Rosenfeld, M. G. & Mayford, M. CBP histone acetyltransferase activity is a critical component of memory consolidation. *Neuron* 42, 961-972 (2004).
18. Vecsey, C. G., et al. Histone deacetylase inhibitors enhance memory and synaptic plasticity via CREB:CBP-dependent transcriptional activation. *J Neurosci* 27, 6128-6140 (2007).
19. Chung, Y. H., et al. Age-related changes in CREB binding protein immunoreactivity in the cerebral cortex and hippocampus of rats. *Brain Res* 956, 312-318 (2002).
20. Trompet, S., et al. Variation in the CBP gene involved in epigenetic control associates with cognitive function. *Neurobiol Aging*.
21. Peleg, S., et al. Altered histone acetylation is associated with age-dependent memory impairment in mice. *Science* 328, 753-756 (2010).
22. Vermaak, D., Wade, P. A., Jones, P. L., Shi, Y. B. & Wolffe, A. P. Functional analysis of the SIN3-histone deacetylase RPD3-RbAp48-histone H4 connection in the *Xenopus* oocyte. *Mol Cell Biol* 19, 5847-5860 (1999).
23. Mayford, M., et al. Control of memory formation through regulated expression of a CaMKII transgene. *Science* 274, 1678-1683 (1996).
24. Resnick, S. M., Trotman, K. M., Kawas, C. & Zonderman, A. B. Age-associated changes in specific errors on the Benton Visual Retention Test. *J Gerontol B Psychol Sci Soc Sci* 50, P171-178 (1995).
25. Schacter, D. L., Cooper, L. A. & Valdiserri, M. Implicit and explicit memory for novel visual objects in older and younger adults. *Psychol Aging* 7, 299-308 (1992).
26. Grady, C. L., et al. Age-related reductions in human recognition memory due to impaired encoding. *Science* 269, 218-221 (1995).
27. Moss, M. B., Rosene, D. L. & Peters, A. Effects of aging on visual recognition memory in the rhesus monkey. *Neurobiol Aging* 9, 495-502 (1988).
28. Rapp, P. R. & Amaral, D. G. Evidence for task-dependent memory dysfunction in the aged monkey. *J Neurosci* 9, 3568-3576 (1989).
29. Erickson, C. A. & Barnes, C. A. The neurobiology of memory changes in normal aging. *Exp Gerontol* 38, 61-69 (2003).
30. Morris, R. G., Garrud, P., Rawlins, J. N. & O'Keefe, J. Place navigation impaired in rats with hippocampal lesions. *Nature* 297, 681-683 (1982).
31. Lin, W., Celik, A. & Paczynski, R. P. Regional cerebral blood volume: a comparison of the dynamic imaging and the steady state methods. *J Magn Reson Imaging* 9, 44-52 (1999).
32. Moreno, H., Brown, T. & SA, S. An MRI technique for mapping cerebral blood volume longitudinally in mice. *NMR in Biomedicine* In Press (2006).
33. Gaisler-Salomon, I., et al. Glutaminase-deficient mice display hippocampal hypoactivity, insensitivity to pro-psychotic drugs and potentiated latent inhibition: relevance to schizophrenia. *Neuropsychopharmacology* 34, 2305-2322 (2009).
34. Wu, W. & Small, S. A. Imaging the earliest stages of Alzheimer's disease. *Curr Alzheimer Res* 3, 529-539 (2006).
35. Chen, Y. J., et al. Type III neuregulin-1 is required for normal sensorimotor gating, memory-related behaviors, and corticostriatal circuit components. *J Neurosci* 28, 6872-6883 (2008).

36. Zhang, Q., Vo, N. & Goodman, R. H. Histone binding protein RbAp48 interacts with a complex of CREB binding protein and phosphorylated CREB. *Mol Cell Biol* 20, 4970-4978 (2000).
37. Kellendonk, C., et al. Transient and selective overexpression of dopamine D2 receptors in the striatum causes persistent abnormalities in prefrontal cortex functioning. *Neuron* 49, 603-615 (2006).
38. Mutant mice and neuroscience: recommendations concerning genetic background. Banbury Conference on genetic background in mice. *Neuron* 19, 755-759 (1997).
39. Trifilieff, P., et al. Foreground contextual fear memory consolidation requires two independent phases of hippocampal ERK/CREB activation. *Learn Mem* 13, 349-358 (2006).
40. Malleret, G., Hen, R., Guillou, J. L., Segu, L. & Buhot, M. C. 5-HT1B receptor knock-out mice exhibit increased exploratory activity and enhanced spatial memory performance in the Morris water maze. *J Neurosci* 19, 6157-6168 (1999).
41. Bevins, R. A. & Besheer, J. Object recognition in rats and mice: a one-trial non-matching-to-sample learning task to study 'recognition memory'. *Nat Protoc* 1, 1306-1311 (2006).
42. Theis, M., Si, K. & Kandel, E. R. Two previously undescribed members of the mouse CPEB family of genes and their inducible expression in the principal cell layers of the hippocampus. *Proc Natl Acad Sci USA* 100, 9602-9607 (2003).

What is claimed is:

1. A transgenic mouse whose genome comprises:
   i) a nucleic acid sequence encoding a dominant negative RbAp48 (RbAp48-DN) protein operably linked to a tetracycline promoter; and
   ii) a nucleic acid sequence encoding a tetracycline controlled transactivator (tTA) operably linked to a CaM Kinase IIa promoter, wherein expression of the RbAp48-DN is restricted to the forebrain, and wherein said mouse is capable of having a memory deficit as compared to a wild-type mouse upon administration of tetracycline.

2. The transgenic mouse of claim 1, wherein said RbAp48-DN lacks the N-terminal 54 amino acids of RbAp48.

3. A method for identifying an agent that slows, inhibits, or prevents a memory deficit, the method comprising:
   a) administering tetracycline to the mouse of claim 1 such that expression of RbAp48-DN is induced in the brain and a memory deficit occurs;
   b) administering an agent to the mouse of step a);
   c) determining the memory of the mouse of step b), wherein increased memory as compared to a transgenic mouse of claim 1 not given the agent indicates the agent slows, inhibits, or prevents a memory deficit.

4. The method of claim 3, wherein the agent increases RbAp48 expression.

5. The method of claim 3, wherein the agent is epicatechin.

6. The method of claim 3, wherein the agent is a histone acetyl transferase.

7. The method of claim 3, wherein the agent is a histone deactylase (HDAC) inhibitor.

8. The method of claim 7, wherein the HDAC inhibitor is selected from the group consisting of belinostat, mocetinostat, panobinostat, dacinostat, 4-Dimethylamino-N-(6-hydoxycarbamoylhexyl)-beinzamide, N-(2-aminophenyl)-N'-phenyl-octanediamide, etinostat, tacedinaline, suberoylanilide hydroxamic acid (SAHA), trichostatin A, traproxin B, valproic acid, (E)-3-(2-butyl-1-(2-(diethylamino)ethyl)-1H-benzo[d]imidazol-5-yl)-N-hydroxyacrylamide, romidepsin, givinostat, and sulforaphane.

9. The method of claim 3, wherein the agent is a phosphodiesterase inhibitor.

10. The method of claim 9, wherein the phosphodiesterase inhibitor is selected from the group consisting of vinpocetine, erythro-9-(2-hydroxy-3-nonyl)adenine), arofyllin, denbufylline, Drotaverine, etazolate, filaminast, (3R,5R)-5-(3-(cyclopentyloxy)-4-methoxyphenyl)-3-(3-methylbenzyl)piperidin-2-one, ibudilast, irsogladine, mesembrine, roflumilast, rolipram, MEM 1917, MEM 1414.

11. The method of claim 3, wherein the memory is assessed using novel object recognition.

12. The method of claim 3, wherein the memory is assessed using the Morris water maze.

13. The method of claim 3, wherein expression of RbAp48-DN is induced 10 days prior to administering the agent.

14. The method of claim 3, further comprising determining the cerebral blood volume (cbv) in the dentate gyrus in the mouse of step b), wherein increased cbv as compared to a transgenic mouse of claim 1 not given the agent further indicates the agent slows, inhibits, or prevents a memory deficit.

* * * * *

SEQUENCE LISTING

<160> NUMBER OF SEQ ID NOS: 3

<210> SEQ ID NO 1
<211> LENGTH: 425
<212> TYPE: PRT
<213> ORGANISM: Homo sapiens

<400> SEQUENCE: 1

```
Met Ala Asp Lys Glu Ala Ala Phe Asp Asp Ala Val Glu Glu Arg Val
1               5                   10                  15

Ile Asn Glu Glu Tyr Lys Ile Trp Lys Lys Asn Thr Pro Phe Leu Tyr
            20                  25                  30

Asp Leu Val Met Thr His Ala Leu Glu Trp Pro Ser Leu Thr Ala Gln
        35                  40                  45

Trp Leu Pro Asp Val Thr Arg Pro Glu Gly Lys Asp Phe Ser Ile His
    50                  55                  60

Arg Leu Val Leu Gly Thr His Thr Ser Asp Glu Gln Asn His Leu Val
65                  70                  75                  80

Ile Ala Ser Val Gln Leu Pro Asn Asp Asp Ala Gln Phe Asp Ala Ser
                85                  90                  95

His Tyr Asp Ser Glu Lys Gly Glu Phe Gly Gly Phe Gly Ser Val Ser
            100                 105                 110

Gly Lys Ile Glu Ile Glu Ile Lys Ile Asn His Glu Gly Glu Val Asn
        115                 120                 125

Arg Ala Arg Tyr Met Pro Gln Asn Pro Cys Ile Ile Ala Thr Lys Thr
    130                 135                 140

Pro Ser Ser Asp Val Leu Val Phe Asp Tyr Thr Lys His Pro Ser Lys
145                 150                 155                 160

Pro Asp Pro Ser Gly Glu Cys Asn Pro Asp Leu Arg Leu Arg Gly His
                165                 170                 175

Gln Lys Glu Gly Tyr Gly Leu Ser Trp Asn Pro Asn Leu Ser Gly His
            180                 185                 190

Leu Leu Ser Ala Ser Asp Asp His Thr Ile Cys Leu Trp Asp Ile Ser
        195                 200                 205

Ala Val Pro Lys Glu Gly Lys Val Val Asp Ala Lys Thr Ile Phe Thr
    210                 215                 220

Gly His Thr Ala Val Val Glu Asp Val Ser Trp His Leu Leu His Glu
225                 230                 235                 240

Ser Leu Phe Gly Ser Val Ala Asp Asp Gln Lys Leu Met Ile Trp Asp
                245                 250                 255

Thr Arg Ser Asn Asn Thr Ser Lys Pro Ser His Ser Val Asp Ala His
            260                 265                 270
```

```
Thr Ala Glu Val Asn Cys Leu Ser Phe Asn Pro Tyr Ser Glu Phe Ile
        275                 280                 285
Leu Ala Thr Gly Ser Ala Asp Lys Thr Val Ala Leu Trp Asp Leu Arg
        290                 295                 300
Asn Leu Lys Leu Lys Leu His Ser Phe Glu Ser His Lys Asp Glu Ile
305                 310                 315                 320
Phe Gln Val Gln Trp Ser Pro His Asn Glu Thr Ile Leu Ala Ser Ser
                325                 330                 335
Gly Thr Asp Arg Arg Leu Asn Val Trp Asp Leu Ser Lys Ile Gly Glu
                340                 345                 350
Glu Gln Ser Pro Glu Asp Ala Glu Asp Gly Pro Pro Glu Leu Leu Phe
            355                 360                 365
Ile His Gly Gly His Thr Ala Lys Ile Ser Asp Phe Ser Trp Asn Pro
        370                 375                 380
Asn Glu Pro Trp Val Ile Cys Ser Val Ser Glu Asp Asn Ile Met Gln
385                 390                 395                 400
Val Trp Gln Met Ala Glu Asn Ile Tyr Asn Asp Glu Asp Pro Glu Gly
                405                 410                 415
Ser Val Asp Pro Glu Gly Gln Gly Ser
                420                 425

<210> SEQ ID NO 2
<211> LENGTH: 18
<212> TYPE: DNA
<213> ORGANISM: Mus musculus

<400> SEQUENCE: 2
tcctgcaacg cacgaccc                                                       18

<210> SEQ ID NO 3
<211> LENGTH: 20
<212> TYPE: DNA
<213> ORGANISM: Mus musculus

<400> SEQUENCE: 3
caaagtctgt gcctcaaacc                                                     20
```